(12) United States Patent
Thibodeau

(10) Patent No.: US 8,603,175 B2
(45) Date of Patent: Dec. 10, 2013

(54) METHOD OF INSERTING SURGICAL IMPLANT WITH GUIDING RAIL

(75) Inventor: Lee L. Thibodeau, Cumberland, ME (US)

(73) Assignee: Stryker Spine (FR)

( * ) Notice: Subject to any disclaimer, the term of this patent is extended or adjusted under 35 U.S.C. 154(b) by 474 days.

(21) Appl. No.: 12/894,946

(22) Filed: Sep. 30, 2010

(65) Prior Publication Data
US 2012/0083885 A1    Apr. 5, 2012

(51) Int. Cl.
*A61F 2/44*    (2006.01)

(52) U.S. Cl.
USPC .................................................. 623/17.16

(58) Field of Classification Search
USPC .............................. 623/17.11–17.16; 606/279
See application file for complete search history.

(56) References Cited

U.S. PATENT DOCUMENTS

| | | |
|---|---|---|
| 4,714,469 A | 12/1987 | Kenna |
| 5,649,931 A | 7/1997 | Bryant et al. |
| 5,782,830 A | 7/1998 | Farris |
| 6,066,174 A | 5/2000 | Farris |
| 6,159,215 A | 12/2000 | Urbahns et al. |
| 6,261,296 B1 | 7/2001 | Aebi et al. |
| 6,562,072 B1 | 5/2003 | Fuss et al. |
| 6,579,318 B2 | 6/2003 | Varga et al. |
| 6,613,090 B2 | 9/2003 | Fuss et al. |
| 6,699,288 B2 | 3/2004 | Moret |
| 6,719,794 B2 | 4/2004 | Gerber et al. |
| D493,225 S | 7/2004 | Varga et al. |
| 6,764,491 B2 | 7/2004 | Frey et al. |
| D494,274 S | 8/2004 | Varga et al. |
| 6,830,570 B1 | 12/2004 | Frey et al. |
| D501,555 S | 2/2005 | Varga et al. |
| 6,852,127 B2 | 2/2005 | Varga et al. |
| 6,984,245 B2 | 1/2006 | McGahan et al. |
| 6,987,245 B2 | 1/2006 | Sanpei et al. |
| 7,060,073 B2 | 6/2006 | Frey et al. |
| 7,060,096 B1 | 6/2006 | Schopf et al. |
| 7,137,997 B2 | 11/2006 | Paul |
| 7,226,483 B2 | 6/2007 | Gerber et al. |
| 7,235,082 B2 | 6/2007 | Bartish et al. |
| 7,361,193 B2 | 4/2008 | Frey et al. |
| 7,470,273 B2 | 12/2008 | Dougherty-Shah |
| 7,479,160 B2 | 1/2009 | Branch et al. |
| 7,481,812 B2 | 1/2009 | Frey et al. |

(Continued)

FOREIGN PATENT DOCUMENTS

| WO | 2008039222 A1 | 4/2008 |
|---|---|---|
| WO | 2008/088777 A2 | 7/2008 |

OTHER PUBLICATIONS

AVS Navigator Surgical Technique, Stryker Spine, 2010.

(Continued)

*Primary Examiner* — Matthew Lawson
(74) *Attorney, Agent, or Firm* — Lerner, David, Littenberg, Krumholz & Mentlik, LLP

(57) ABSTRACT

A prosthetic intervertebral spacer includes a body and an interface extending away from the body for use during implantation of the spacer. The interface can be a rail including a neck portion connected to the body and a lip portion connected to the neck portion. The lip portion can be wider than the neck portion in a direction extending between the top and bottom surfaces of the implant. Methods of implanting the spacer and tools used during such procedure are also provided.

44 Claims, 20 Drawing Sheets

(56) References Cited

U.S. PATENT DOCUMENTS

| | | |
|---|---|---|
| 7,500,991 B2 | 3/2009 | Bartish, Jr. et al. |
| 7,575,580 B2 | 8/2009 | Lim et al. |
| 7,591,852 B2 | 9/2009 | Prosser |
| 7,632,281 B2 | 12/2009 | Errico et al. |
| 7,635,371 B2 | 12/2009 | McGahan et al. |
| 7,658,766 B2 | 2/2010 | Melkent et al. |
| 7,717,961 B2 | 5/2010 | Lambrecht et al. |
| 7,749,273 B2 | 7/2010 | Cauthen, III et al. |
| 7,806,932 B2 | 10/2010 | Webb et al. |
| 7,976,549 B2 | 7/2011 | Dye et al. |
| 7,998,215 B2 | 8/2011 | Frey et al. |
| 8,252,060 B2 | 8/2012 | Hansell et al. |
| 2002/0065560 A1 | 5/2002 | Varga et al. |
| 2002/0165612 A1 | 11/2002 | Gerber et al. |
| 2003/0040798 A1 | 2/2003 | Michelson |
| 2004/0030346 A1 | 2/2004 | Frey et al. |
| 2004/0186574 A1 | 9/2004 | Varga et al. |
| 2004/0186575 A1 | 9/2004 | Varga et al. |
| 2004/0254644 A1 | 12/2004 | Taylor |
| 2005/0096745 A1 | 5/2005 | Andre et al. |
| 2005/0283244 A1 | 12/2005 | Gordon et al. |
| 2005/0283245 A1 | 12/2005 | Gordon et al. |
| 2006/0004376 A1 | 1/2006 | Shipp et al. |
| 2006/0178746 A1 | 8/2006 | Bartish et al. |
| 2006/0212119 A1 | 9/2006 | Varga et al. |
| 2006/0212120 A1 | 9/2006 | McGahan et al. |
| 2006/0229627 A1 | 10/2006 | Hunt et al. |
| 2006/0235426 A1 | 10/2006 | Lim et al. |
| 2006/0241761 A1 | 10/2006 | Gately |
| 2006/0276800 A1 | 12/2006 | Lee et al. |
| 2007/0067035 A1 | 3/2007 | Falahee |
| 2007/0073400 A1 | 3/2007 | Paul |
| 2007/0073405 A1 | 3/2007 | Verhulst et al. |
| 2007/0093850 A1 | 4/2007 | Harris et al. |
| 2007/0093897 A1 | 4/2007 | Gerbec et al. |
| 2007/0118223 A1 | 5/2007 | Allard et al. |
| 2007/0142843 A1 | 6/2007 | Dye |
| 2007/0162128 A1 | 7/2007 | DeRidder et al. |
| 2007/0208343 A1 | 9/2007 | Magerl et al. |
| 2007/0213737 A1 | 9/2007 | Schermerhorn et al. |
| 2007/0213826 A1 | 9/2007 | Smith et al. |
| 2007/0225726 A1 | 9/2007 | Dye et al. |
| 2007/0225808 A1 | 9/2007 | Warnick |
| 2007/0282441 A1 | 12/2007 | Stream et al. |
| 2008/0009880 A1 | 1/2008 | Warnick et al. |
| 2008/0058933 A1 | 3/2008 | Garner et al. |
| 2008/0065082 A1 | 3/2008 | Chang et al. |
| 2008/0065219 A1 | 3/2008 | Dye |
| 2008/0077150 A1 | 3/2008 | Nguyen |
| 2008/0077153 A1 | 3/2008 | Pernsteiner et al. |
| 2008/0077241 A1 | 3/2008 | Nguyen |
| 2008/0091211 A1 | 4/2008 | Gately |
| 2008/0097435 A1 | 4/2008 | DeRidder et al. |
| 2008/0097454 A1 | 4/2008 | DeRidder et al. |
| 2008/0109005 A1 | 5/2008 | Trudeau et al. |
| 2008/0119935 A1 | 5/2008 | Alvarez |
| 2008/0140085 A1* | 6/2008 | Gately et al. .................... 606/99 |
| 2008/0221694 A1 | 9/2008 | Warnick et al. |
| 2008/0224694 A1 | 9/2008 | Bidenbach et al. |
| 2008/0249623 A1* | 10/2008 | Bao et al. .................. 623/17.11 |
| 2008/0255574 A1 | 10/2008 | Dye |
| 2008/0262623 A1 | 10/2008 | Bagga et al. |
| 2008/0269901 A1 | 10/2008 | Baynham et al. |
| 2008/0287957 A1 | 11/2008 | Hester et al. |
| 2008/0306488 A1 | 12/2008 | Altarac et al. |
| 2008/0306489 A1 | 12/2008 | Altarac et al. |
| 2009/0030423 A1 | 1/2009 | Puno |
| 2009/0054991 A1 | 2/2009 | Biyani et al. |
| 2009/0105832 A1 | 4/2009 | Allain et al. |
| 2009/0105836 A1 | 4/2009 | Frey et al. |
| 2009/0112217 A1 | 4/2009 | Hester |
| 2009/0112220 A1 | 4/2009 | Kraus |
| 2009/0138055 A1 | 5/2009 | Altarac et al. |
| 2009/0143829 A1 | 6/2009 | Shluzas |
| 2009/0143859 A1 | 6/2009 | McClellan, III et al. |
| 2009/0157186 A1 | 6/2009 | Magerl |
| 2009/0177285 A1 | 7/2009 | Frey et al. |
| 2009/0182428 A1 | 7/2009 | McClellan, III et al. |
| 2009/0187246 A1 | 7/2009 | Foley |
| 2009/0198246 A1 | 8/2009 | Lim et al. |
| 2009/0222092 A1 | 9/2009 | Davis et al. |
| 2009/0228110 A1 | 9/2009 | McClintock |
| 2009/0234364 A1 | 9/2009 | Crook |
| 2009/0248163 A1 | 10/2009 | King et al. |
| 2009/0265008 A1 | 10/2009 | Thibodeau |
| 2009/0299479 A1 | 12/2009 | Jones et al. |
| 2010/0094422 A1 | 4/2010 | Hansell et al. |
| 2010/0100141 A1 | 4/2010 | de Villiers et al. |
| 2010/0137922 A1 | 6/2010 | Hunt et al. |
| 2010/0191337 A1 | 7/2010 | Zamani et al. |
| 2010/0256759 A1* | 10/2010 | Hansell et al. ............. 623/17.11 |
| 2011/0106259 A1 | 5/2011 | Lindenmann et al. |

OTHER PUBLICATIONS

International Search Report, PCT/US2011/053633, dated Jan. 27, 2012.

International Search Report, PCT/US2011/53629, dated Jan. 18, 2012.

International Search Report and Written Opinion, PCT/US2011/53637, dated Feb. 23, 2012.

* cited by examiner

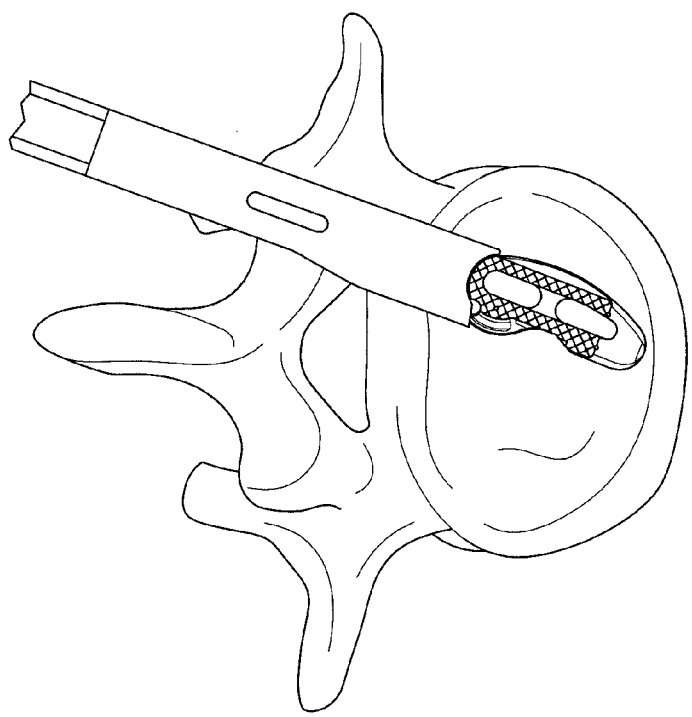
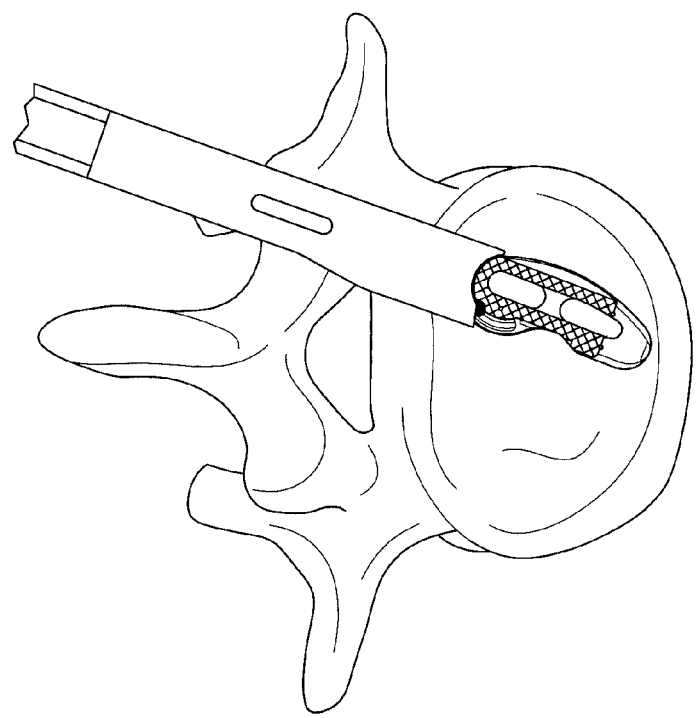
FIG. 16A
FIG. 16B

METHOD OF INSERTING SURGICAL IMPLANT WITH GUIDING RAIL

BACKGROUND OF THE INVENTION

The present invention relates to spinal implants and methods of implanting such implants. More particularly, the present invention relates to a spinal implant having a guiding rail for cooperating with an insertion instrument, as well as the methods associated with implanting that implant.

Back pain can be caused by many different things, including any one of several problems that affect the intervertebral discs of the spine. These disc problems include, for instance, degeneration, bulging, herniation, thinning of a disc, and abnormal movement, and the pain that is experienced is generally attributable to friction or pressure that inevitably occurs when one adjacent vertebra exerts uneven pressure or when both adjacent vertebrae exert such pressure on the disc. Oftentimes, disc problems lead to the vertebrae impinging on one of the very many nerves located in the spinal column.

One surgical method commonly utilized to correct such disc problems is a fusion procedure where a surgeon fuses together adjacent vertebrae in single or multiple levels. Different methods (as well as apparatus for use in those methods) for such surgery have been developed for performance on cervical, thoracic, or lumbar vertebral bodies. These fusion procedures will be referred to herein as interbody fusion or "IF." Traditional IF techniques generally involve removing at least a portion of the troublesome disc from the patient, inserting a spinal implant device into the space to hold the graft material in place and to support the vertebrae while solid bone mass forms therebetween, and adding bone graft material into the interbody space between the vertebrae that flank the disc. Oftentimes, the steps of inserting an implant and bone graft material involve first packing the implant with the bone graft material, and thereafter implanting that construct.

While IF is a long-established technique for correcting the aforementioned disc problems, it is one that is constantly updated. For instance, different implants have been created to suit specific needs, and methods involving the insertion of such implants and the preparation of the vertebrae to receive same are constantly evolving. One major issue that has existed and will continue to exist is the fact that visibility to the surgical site is often hindered by the patient anatomy. For instance, in the cervical section of the spine, the vertebral bodies are rather small and surrounding patient anatomy, such as the esophagus and other body parts, makes access to and visibility of the surgical site rather difficult. This often hinders the surgeon in properly positioning an implant with respect to the vertebrae. Furthermore, in many IF procedures, the required manipulation of the patient anatomy, distraction of the vertebral bodies, and preparation of the vertebral bodies often results in significant scar tissue being formed in the patient. This can be detrimental when performing any subsequently required spinal procedures.

Thus, there exists a need for a spinal implant and method of using the implant that improves upon these shortcomings.

BRIEF SUMMARY OF THE INVENTION

A first aspect of the present invention is a prosthetic intervertebral spacer. In accordance with one embodiment of this first aspect, the spacer includes a body having a front end, a rear end, an anterior side, a posterior side, a top surface, a bottom surface, and an arcuate interface extending away from the body and being connected to the rear end and the posterior side of the body.

In accordance with other embodiments of the first aspect, the interface may include a rail including a neck portion connected to the body and a lip portion connected to the neck portion. The lip portion may be wider than the neck portion in the direction extending between the top and bottom surfaces. The neck and lip portions of the interface may form a T shape. Additionally, a notch may be included in the interface, thereby separating the rail into a first rail segment and a second rail segment. The first rail segment may be disposed on the rear end of the spacer, and the second rail segment may be disposed on the posterior side of the spacer. The notch may extend in a direction substantially parallel to a longitudinal axis of the spacer.

In accordance with still other embodiments of the first aspect, the rear end of the spacer may be curved, so that in certain cases, the curves of the rear end and the arcuate interface may lie on concentric circles. In other embodiments, the front end may be curved, and may include a steering element configured to mate with an adjacent vertebral body to cause rotation of the spacer during insertion. In certain embodiments, the steering element may be a fin or a crease, and may be disposed at an angle with respect to a longitudinal axis of the spacer. Still further, the spacer may include at least one aperture extending between the upper and lower surfaces. The aperture may allow for bone growth inducing substances to be placed therein.

A second aspect of the present invention is another prosthetic intervertebral spacer. In accordance with one embodiment of the second aspect, the spacer includes a body defined by an outer wall having a convexly curved front end, a convexly curved rear end, a convex anterior side, a concave posterior side, a top surface, and a bottom surface. The spacer further includes an arcuate interface protruding from the outer wall and being connected to the rear end and the posterior side of the body, where the interface is a rail including a neck portion connected to the body and a lip portion connected to the neck portion. The lip portion has a first dimension greater than a second dimension of the neck portion, and the outer wall has a third dimension greater than the first dimension, the first and third dimensions extending between the top and bottom surfaces.

In accordance with other embodiments of this second aspect, the rail may further include a notch separating the rail into first and second rail segments. The notch may extend in a direction substantially parallel to the longitudinal axis of the spacer. The first rail segment may be disposed on the rear end of the spacer, and the second rail segment may be disposed on the posterior side of the spacer. Further, the neck portion and lip portion of the interface may form a T shape.

In other embodiments according to the second aspect, the front end may include a steering element configured to mate with an adjacent vertebral body to cause rotation of the spacer. The steering element may be a fin or a crease. Additionally, the steering element may be disposed at an angle with respect to the longitudinal axis of the spacer. Finally, the spacer may include at least one aperture extending between the upper and lower surfaces. The aperture may allow for bone growth inducing substances to be placed therein.

A third aspect of the present invention is another prosthetic intervertebral spacer. This spacer according to the third aspect may include a body having a front end, a rear end, an anterior side, a posterior side, and a longitudinal axis. The front end preferably mates with the anterior side at a transition portion that is curved, the transition portion being configured to interact with an annulus fibrosis of an intervertebral disc to cause rotation in the spacer during insertion of the spacer. The spacer may further include an arcuate interface extending away from the body and being connected to the rear end and the posterior side of the body. In certain embodiments, the interface may be a rail including a neck portion connected to the body and a lip portion connected to the neck portion, the lip portion being wider than the neck portion in the direction extending between the top and bottom surfaces.

A fourth aspect of the present invention is a surgical tool for inserting and positioning a prosthetic intervertebral spacer in the intervertebral disc space between two adjacent vertebrae. In accordance with one embodiment of the fourth aspect, the tool includes a grasping portion including first and second arms having proximal and distal ends, the distal ends being separated by a first dimensions; a sleeve having an inner surface, the sleeve being slidably disposed about the grasping portion, at least the portion of the inner surface having an inner dimension less than the first dimension; a handle portion connected to the proximal ends in the first and second arms, the handle portion having a rod actuator and a sleeve actuator, the sleeve actuator connected to the sleeve to slide the sleeve with respect to the first and second arms; and a rod having a first end disposed adjacent the distal ends of the first and second arms and a second end, the rod actuator connected to the second end to slide the rod with respect with to the grasping portion.

In accordance with other embodiments of the fourth aspect of the present invention, the first and second arms may be flexibly connected to the handle portion such that the distal ends of the first and second arms can move toward and away from another. Further, the first and second arms may also include proximal ends separate by a second distance less than the first distance. Each of the distal ends of the first and second arms may include a projection facing toward the opposite arm for engagement to an interface of the spacer. The distal ends of the first and second arms may be curved to mate with the inner face of the spacer.

In still further embodiments, the inner dimension may be greater than the second distance. The handle portion may include a grip and a shaft portion, the shaft portion having a proximal end connected to the grip and a distal end connected to the grasping portion. Likewise, the sleeve actuator may include a rotatable knob disposed on the handle portion. Still further, the rod actuator may include a slidable switch disposed on the handle portion and a screw for locking the slidable switch with respect to the handle portion.

A fifth aspect of the present invention is a method of using a surgical tool for inserting and positioning a prosthetic intervertebral spacer in the intervertebral disc space between two adjacent vertebrae. In accordance with one embodiment of this aspect, the method may include the steps of providing a surgical tool including a grasping portion having first and second arms having proximal and distal ends, the distal ends being separated by a first dimension; a sleeve having an inner surface, the sleeve being slidably disposed about the grasping portion, at least a portion of the inner surface having an inner dimension less than the first dimension; a handle portion connected to the proximal ends of the first and second arms, the handle portion having a rod actuator and a sleeve actuator, the sleeve actuator connected to the sleeve to slide the sleeve with respect to the first and second arms; and a rod having a first end disposed adjacent the distal ends of the first and second arms and a second end, the rod actuator connected to the second end to slide the rod with respect to the grasping portion. The method may also include the steps of positioning distal ends of the first and second arms adjacent in interface of an intervertebral spacer, moving the sleeve such that the portion of the inner surface to the sleeve having the inner dimension overlaps the distal ends of the first and second arms, thereby engaging the tool to the interface of the spacer, and engaging the first end of the rod to a notch in the spacer.

In accordance with other embodiments of the fifth aspect, the method may further include the steps of inserting the spacer into the intervertebral disc space, disengaging the first end of the rod from the notch, and/or further inserting the spacer into the intervertebral space when the rod is disengaged from the notch. The tool may be configured to slide along the interface of the spacer when engaged with the spacer, where the step of further inserting the spacer includes sliding the tool along the interface of the spacer while the spacer rotates in the intervertebral disc space. Relative rotation of the spacer may be prevented when the rod is engaged to the notch and permitted when the rod is disengaged from the notch. The step of disengaging may be conducted when the spacer contacts a portion of an annulus fibrosis in the anterior portion of the intervertebral disc space.

In further embodiments, the method of the fifth aspect may further include the step of forming a hole through only a portion of the annulus fibrosis while leaving the remainder of the annulus fibrosis in tact, where the step of inserting includes inserting the spacer through the hole. The step of moving the sleeve may include actuating the sleeve actuator. The method may further include the step of tightening the grip of the tool on the spacer by rotating a rotatable knob of the sleeve actuator. The step of engaging the first end of the rod may include actuating a rod actuator. The step of actuating may include sliding a slidable switch through the road actuator with respect to the handle portion and locking the slidable switch to the handle portion by tightening the screw of the rod actuator. The method may further include the step of disengaging the first end of the rod from the notch by loosening the screw and sliding the slidable switch with respect to the handle portion. The first and second arms of the tool may be flexibly connected to the handle portion and the step of moving the sleeve may cause the distal ends of the first and second arms to move toward one another. In still further embodiments, each of the distal ends of the first and second arms may include a projection facing toward the opposite arm for engagement to an interface of the spacer, and the step of moving the sleeve may cause the distal ends of the first and second arms to engage the projections to mating channels in the interface of the spacer. Additionally, the handle portion may include a grip and a shaft portion, the shaft portion having a proximal end connected to the grip and a distal end connected to the grasping portion.

A sixth aspect of the present invention is another method of using a surgical tool for inserting and positioning a prosthetic intervertebral spacer in the intervertebral disc space between two adjacent vertebrae. The method according to the sixth aspect may include the steps of positioning distal ends of first and second arms with a surgical tool adjacent an interface of intervertebral spacer, the distal ends being separated by a first dimension, moving a sleeve of the tool such that a portion of an inner surface of the sleeve having an inner dimension less than the first dimension overlapped the distal ends of the first and second arms, thereby engaging the tool to the interface of the spacer, and engaging a rod of the tool to a notch in the spacer.

In accordance with embodiments of the sixth aspect, the method may further include the steps of inserting the spacer into the intervertebral space, disengaging the rod from the notch, and/or further inserting the spacer into the intervertebral space when the rod is disengaged from the notch. In further embodiments, the tool may be configured to slide along the interface of the spacer when engaged with the spacer, with the step of further inserting the spacer includes sliding the tool along the interface of the spacer while the spacer rotates in the intervertebral disc space. Relative rotation between the spacer and the tool may be prevented when the rod is engaged to the notch and permitted when the rod is disengaged from the notch. The step of disengaging may be conducted when the spacer contacts the annulus fibrosis in the anterior portion of the intervertebral disc space.

Further, the method of this sixth aspect, may further comprise the step of forming a hole through only a portion of the annulus fibrosis while leaving the remainder of the annulus fibrosis in tact, where the step of inserting includes inserting the spacer through the hole. The step of moving the sleeve may include actuating the sleeve actuator of the tool thereby tightening the grip of the tool on the spacer by rotating a rotatable knob of the sleeve aperture. The step of engaging the rod may include actuating the rod actuator of the tool, including sliding the slidable switch of the rod actuator with respect to the handle portion and locking the slidable switch to the handle portion by tightening a screw of the rod actuator. The method may further comprise the step of disengaging the first end of the rod from the notch by loosening the screw and sliding the slidable switch with respect to the handle portion. The first and second arms of the tool may be flexibly connected to a handle portion of the tool, and the step of moving a sleeve may cause the distal ends of the first and second knobs to move towards one another. Each of the distal ends of the first and second arms may include a projection facing toward the opposite arm for engagement to an interface of the spacer, and the step of moving the sleeve may cause the distal ends of the first and second arms to engage the projections to mating channels in the interface of the spacer.

A seventh aspect of the present invention is a method of inserting and positioning a prosthetic intervertebral spacer in an intervertebral disc space between two adjacent vertebrae. In accordance with one embodiment of the seventh aspect, the method may include the steps of providing a spacer including a body having a front end, a rear end, a longitudinal axis, and an interface extending away from the body and being connected to the rear end of the body, engaging a tool to the interface; inserting the spacer at least partially into the intervertebral disc space by moving the tool along an insertion direction; and allowing the spacer to rotate with respect to the insertion direction within in the intervertebral disc space while continuing to move the tool along the insertion direction.

In accordance with certain embodiments of the seventh aspect, the tool may maintain its engagement to the interface during the steps of inserting and allowing. The step of allowing the spacer to rotate may include allowing the front end to interact with an annulus fibrosis of an intervertebral disc to cause rotation in the spacer with respect to the insertion direction. The method may further include the step of forming a hole through only a portion of the annulus fibrosis while leaving the remainder of the annulus fibrosis in tact, where the step of inserting includes inserting the spacer through the hole. The spacer may be inserted such that the spacer is positioned in an anterior aspect of the intervertebral disc space. The spacer may be inserted to a final position where the longitudinal axis of the spacer is perpendicular to the insertion direction. The longitudinal axis of the spacer may be substantially parallel to a medial lateral axis of the intervertebral disc space. The spacer may be inserted such that the longitudinal axis of the spacer is rotated approximately 80 degrees with respect to the insertion direction. The allowing step may include allowing the tool to slide along the interface during rotation of the spacer. The insertion direction may be substantially parallel to a posterior-anterior axis of the intervertebral disc space. The interface of the spacer may include a notch and the tool may include a rod engageable to the notch, where the method further includes the step of engaging the rod to the notch to prevent relative rotation between the spacer and the tool and the step of disengaging the rod from the notch to allow relative rotation between the spacer and the tool. The allowing step may take place after the rod is disengaged from the notch. The spacer may at least be partially inserted with the rod engaged to the notch and at least partially inserted with the rod from the notch. The body may further include a top surface, a bottom surface, and at least one aperture extending between the top and bottom surfaces, where the method further includes the step of packing bone graft material into the at least one aperture. The spacer may further include a front end having frictional properties that are greater than frictional properties of a rear end in the spacer to aid in the rotation of the spacer within the intervertebral space. The step of allowing the spacer to rotate further may include allowing a steering element disposed on the front end of the spacer to mate with one of the two adjacent vertebral bodies to cause rotation of the spacer with respect to the insertion direction. The steering element may be disposed at an angle with respect to the longitudinal axis. The steering element may be a fin or crease.

An eighth aspect of the present invention is another method of inserting and positioning a prosthetic intervertebral spacer in an intervertebral disc space between two adjacent vertebrae. In accordance with one embodiment of the eighth aspect, the method may include the steps of providing a spacer including a body having a front end, a rear end, a longitudinal axis, and an interface extending away from the body and being connected to the rear end of the body, the interface including a notch; engaging a tool to be interface, the tool including a rod; engaging the rod to the notch to prevent relative rotation between the spacer and the tool; inserting the spacer at least partially into the intervertebral disc space by moving the tool along an insertion direction; disengaging the rod from the notch; inserting the spacer further into the intervertebral disc space after the disengaging step by moving the tool substantially along the insertion direction; and allowing the spacer to rotate with respect to the insertion direction within the intervertebral disc space when the rod is disengaged from the notch while continuing to move the tool along the insertion direction.

In accordance with certain embodiments of the eighth aspect, the method may further include the step of forming a hole through only a portion of an annulus fibrosis while leaving the remainder of the annulus fibrosis intact, where the step of inserting includes inserting the spacer through the hole. The step of allowing the spacer to rotate may include allowing the front end to interact with an annulus fibrosis of an intervertebral disc to cause rotation to the spacer with respect to the insertion direction. The tool may maintain its engagement to the interface during the steps of inserting and allowing. The spacer may be inserted such that the spacer's position in an anterior aspect of the intervertebral disc space. The spacer may be inserted to a final position where the longitudinal axis of the spacer is perpendicular to the insertion direction. The longitudinal axis of the spacer may be substantially parallel to a medial-lateral axis of the intervertebral disc space. The spacer may be inserted such that the longitudinal axis of the spacer is rotated approximately 80 degrees with respect to the insertion direction. The allowing step may include allowing the tool to slide along the interface during rotation of the spacer. The front end of the spacer may include a steering element, and the step of allowing the spacer to rotate further may include allowing the steering element to mate with one of the adjacent vertebral bodies to cause a rotation of the spacer with respect to the insertion direction. The steering element may be disposed at an angle with respect to the longitudinal axis. The steering element may be a fin or crease. The insertion direction may be substantially parallel to a posterior that is entered axially in a vertebral disc space.

Further, the body may include a top surface, a bottom surface, and at least one aperture extending between the top and bottom surfaces, where the method further includes the step of packing bone graft material into the at least one aperture. The spacer may further include a front end having frictional properties that are greater than frictional properties of a rear end of the spacer to aid in the rotation of the spacer within the intervertebral disc space. The first step of inserting may include applying a force to the spacer along a first axis substantially parallel to the longitudinal axis of the spacer, and the second step of inserting may include applying a force to the spacer along a second axis forming an angle with the axis of great than zero degrees.

A ninth aspect of the present invention is another method of inserting and positioning a prosthetic intervertebral spacer in an intervertebral disc space between two adjacent vertebrae. In accordance with one embodiment of the ninth aspect, the method may include the steps of providing a spacer including a body having a front end, a rear end, a longitudinal axis, and an interface extending away from the body and being connected to the rear end of the body; applying a force to a tool engaged to the interface to move the spacer in the intervertebral disc space, the force being directed along an insertion direction; and allowing the front end to interact with an annulus fibrosis of an intervertebral disc to cause rotation in the spacer with respect to the insertion direction while continuing to move the tool along the insertion direction.

In other embodiments of the ninth aspect, the method may further include the step of forming a hole through only a portion of the annulus fibrosis while leaving the remainder of the annulus fibrosis intact, and the step of inserting the spacer through the hole. The engaging between the tool and the interface may be maintained during the steps of applying and allowing. The allowing step may include allowing the tool to slide along the interface during rotation of the spacer. The interface of the spacer may include a notch and the tool may include a rod engaged to the notch, where the method further includes the step of engaging the rod to the notch to prevent relative rotation between the spacer and the tool and the step of disengaging the rod from the notch to allow relative rotation between the spacer and the tool. The allowing step may take place after the rod is disengaged from the notch. The spacer may be at least partially inserted with the rod engaged to the notch and at least partially inserted with the rod disengaged from the notch. The step of allowing may include allowing a steering element disposed on the front end of the spacer to meet with an adjacent vertebral body to cause rotation of the spacer with respect to the insertion direction. The steering element may be disposed at an angle with respect to the longitudinal axis. The steering element may be a fin or a crease. The step of applying may include the insertion direction being substantially parallel to the longitudinal axis of the spacer and the method may further include the step of applying a second force to the spacer along the second axis forming an angle with the longitudinal axis of greater than zero degrees.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIGS. 16a-16g are illustrations depicting various stages of insertion of the spacer shown in FIG. 1 in relation to the insertion tool shown in FIG. 6 and a vertebral body.

DETAILED DESCRIPTION

Figure 1:
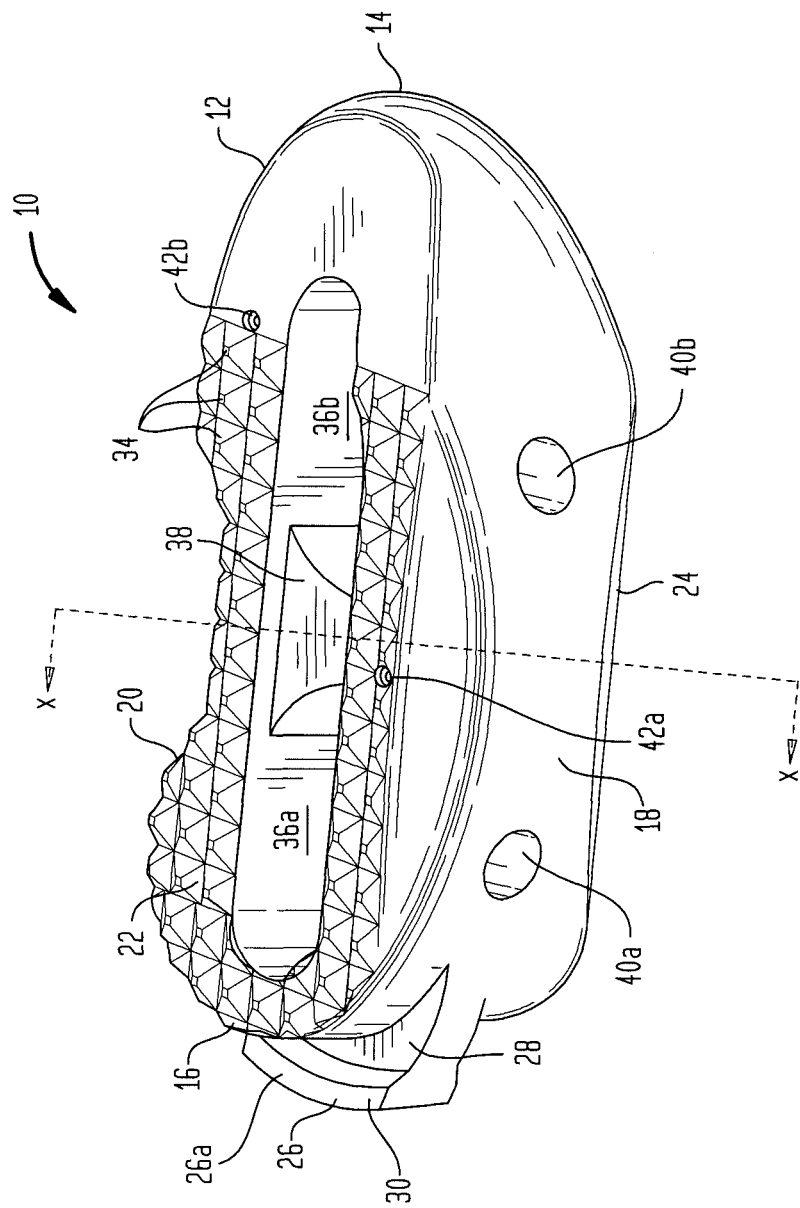
FIG. 1 is a front perspective view of a prosthetic intervertebral spacer in accordance with one embodiment of the present invention.
Figure 2:
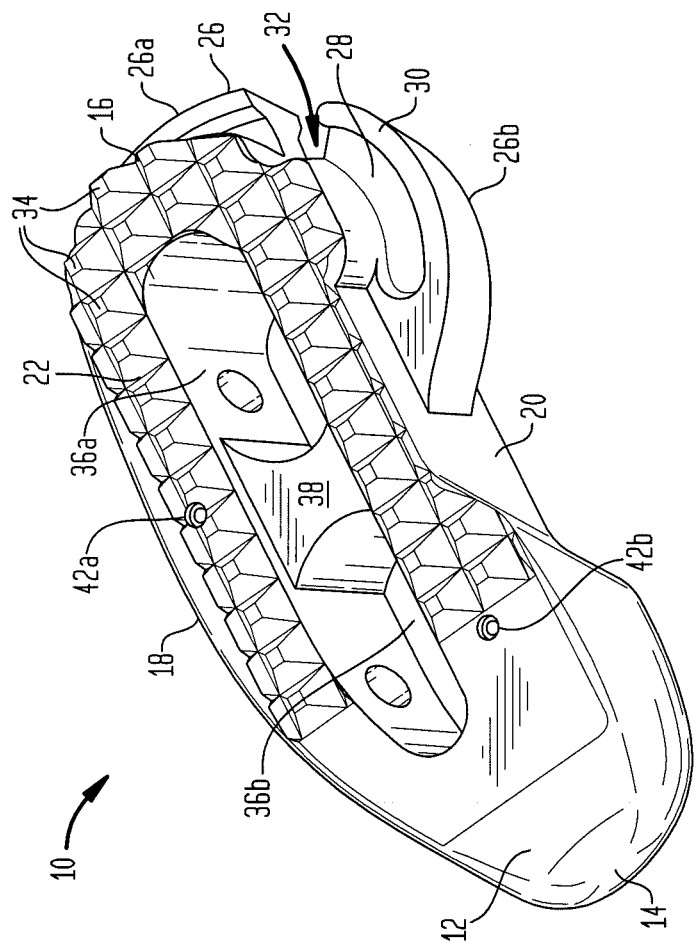
FIG. 2 is a top perspective view of the spacer shown in FIG. 1.
Figure 3:
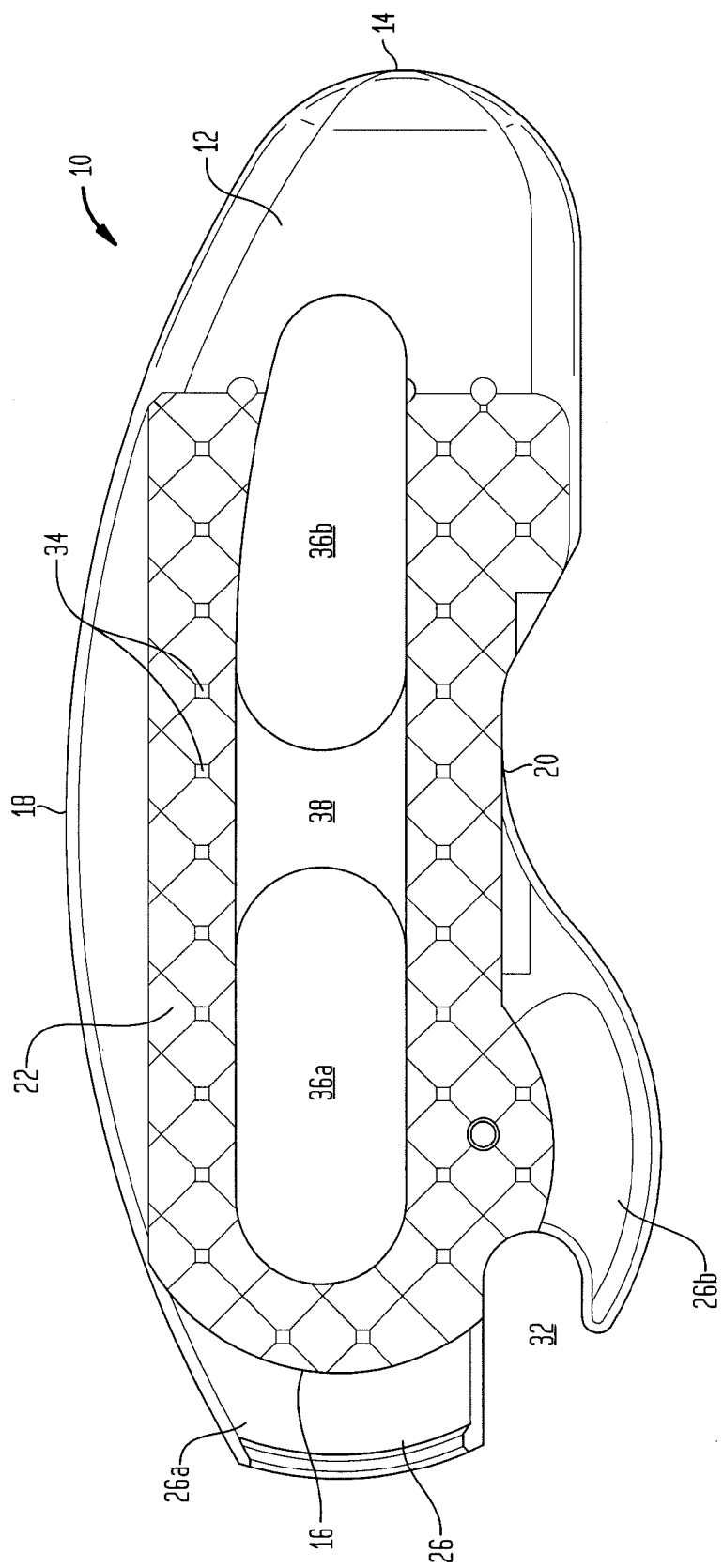
FIG. 3 is a top view of the spacer shown in FIG. 1, the bottom view being a mirror image thereof.
Figure 4:
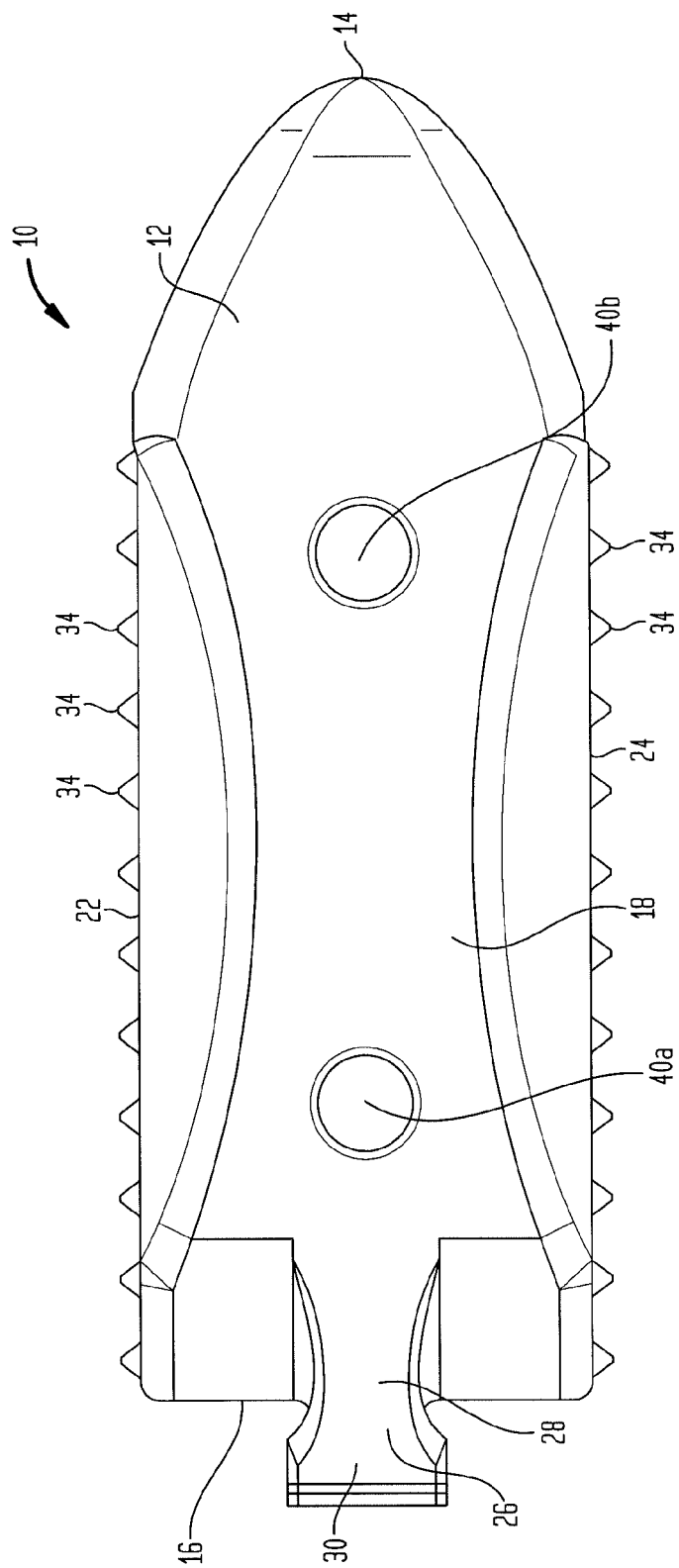
FIG. 4 is a side view of the spacer shown in FIG. 1.

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Referring to FIGS. 1-4, there is shown a prosthetic intervertebral spacer 10 in accordance with one embodiment of the present invention. As shown, spacer 10 includes a body 12, which in turn includes a front end 14, a rear end 16, an anterior side 18, a posterior side 20, a top surface 22, and a bottom surface 24. Spacer 10 further includes an interface 26, including a neck portion 28, a lip portion 30, and a notch 32. Notch 32 separates interface 26 into first and second segments 26a and 26b (best shown in FIGS. 2 and 3), respectively. In the embodiment shown in FIGS. 1-4, interface 26 is arcuate and can best be described as a rail. However, in other embodiments, interface 26 can vary in shape, size, and configuration, with the only limitation being its cooperation with an insertion tool, such as the one discussed more fully below. Likewise, in the embodiments shown in FIGS. 1-4, notch 32 is shown as extending in a direction substantially parallel to a longitudinal axis of spacer 10, and neck portion 28 and lip portion 30 are shown as forming a T-shape. Again, these elements can vary in other embodiments.

Figure 17:
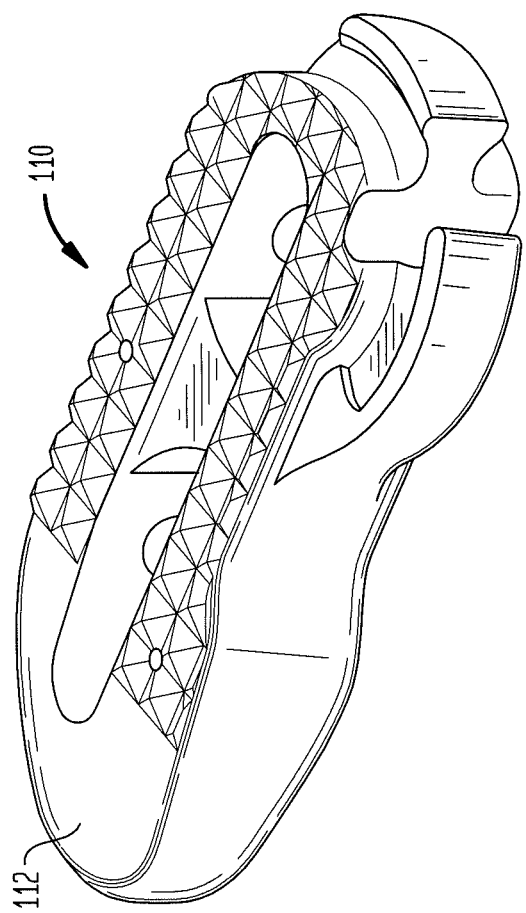
FIG. 17 is a perspective view of a prosthetic intervertebral spacer in accordance with another embodiment of the present invention.

Spacer 10 is preferably constructed of a polymeric material, such as polyetheretherketone ("Peek"). However, spacer 10 may be constructed of practically any materials suitable for implantation in the body of a human. Front end 14 and rear end 16 are shown as being curved, where the curves of the rear end and arcuate interface 26 lie in concentric circles. Again, in other embodiments, this configuration may vary. For instance, it is contemplated to provide a substantially square or rectangular shaped spacer 10. In the embodiment shown in FIGS. 1-4, front end 14 defines a tapered nose for spacer 10. However, in other embodiments, front end 14 may (additional to or in lieu of the tapered nose structure) include a steering element configured to mate with at least one of the adjacent vertebral bodies spacer 10 is designed to be placed between in order to cause rotation of spacer 10 during insertion. Such a steering element may include a fin or crease, and may be disposed at an angle with respect to longitudinal axis of spacer 10. One example spacer 110 of this type is depicted in FIG. 17, in which a steering element 112 takes the form of a crease. Of course, in other embodiments employing such a steering element, other designs may be employed.

In the embodiment shown, top and bottom surfaces 22 and 24 each include a plurality of bone-engaging features in the form of teeth 34. Other features may be employed for aiding in the fixation of spacer 10 to the adjacent vertebrae. Spacer 10 also includes apertures 36a and 36b formed through top and bottom surfaces 22 and 24. Apertures 36a and 36b are separated by a strut 38, which is recessed with respect to both top and bottom surfaces 22 and 24. In other embodiments, strut 38 may be formed flush with top and bottom surfaces 22 and 24, or only recessed with respect to one or the other. Apertures 36a and 36b are preferably designed to receive bone growth material, as will be discussed more fully below. Apertures 36a and 36b also exhibit an oblong shape in order to avoid sharp corners that generally create engineering stresses and may cause harm to the interior patient anatomy. Spacer 10 further includes lateral fenestrations 40a and 40b, which are preferably designed for allowing fusion that develops between the upper and lower vertebrae (through the spacer) to spread laterally as well, and a plurality of vertical markers 42a and 42b, which are preferably constructed of tantalum and press fitted into spacer 10. Markers 42a and 42b make the visual identification of spacer 10 easier through a traditional X-ray technique.

Spacer 10 shown in FIGS. 1-4 preferably includes a length dimension from front end 14 to rear end 16 that is preferably within the range of 15 mm to 40 mm, and more preferably between 26 mm and 31 mm, as well as a length dimension from front end 14 to the end of interface 26 that is preferably within the range of 17 mm to 42 mm, and more preferably between 28 mm and 32 mm. A width dimension from anterior side 18 to posterior side 20 of spacer 10 shown in FIGS. 1-4 is preferably in the range of 8 mm to 16 mm, and more preferably approximately 12 mm. Spacer 10 shown in FIGS. 1-4 also preferably includes a height dimension from top surface 22 to bottom surface 24 within the range of 6 mm to 15 mm. Of course, in other embodiments, spacer 10 may be of any size. For instance, spacers 10 designed for use in the cervical area of the spine may be smaller than spacers 10 designed for use in the thoracic or lumber spine.

Figure 5:
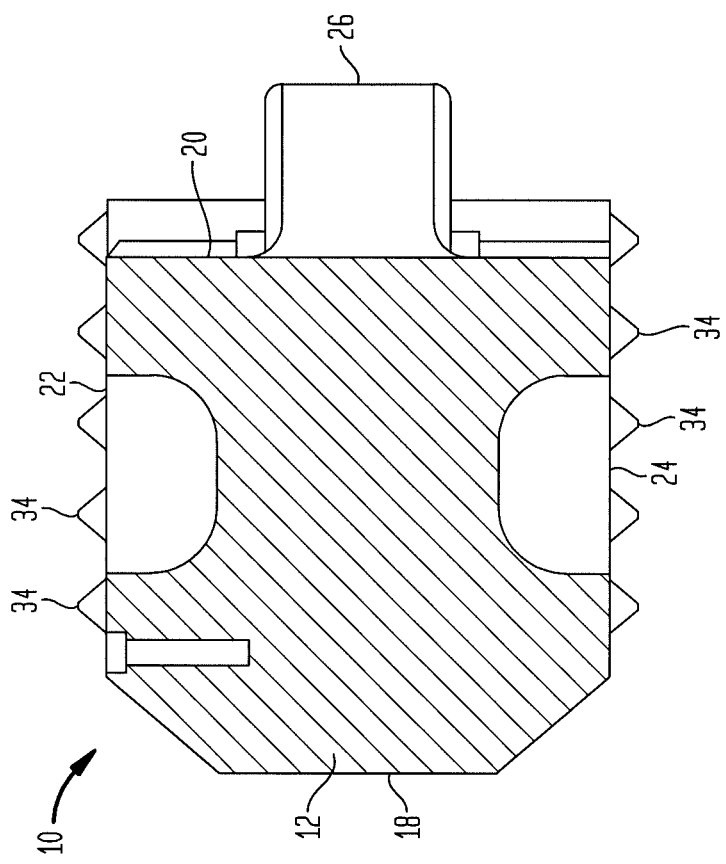
FIG. 5 is a cross-sectional view of a modified version of the spacer shown in FIG. 1, the section being taken through the modified version in a similar fashion to line X-X of FIG. 1.

Although shown in FIGS. 1-4 as having top and bottom surfaces 22 and 24 situated in a parallel fashion with respect to each other, FIG. 5 depicts a version of spacer 10 exhibiting top and bottom surfaces 22 and 24 that taper from anterior side 18 to posterior side 20. This tapered construction preferably aids in restoring the natural lordotic angle of the adjacent vertebrae. The angle of each taper is preferably within the range of zero to ten degrees with respect to the midplane of spacer 10 to comport with the natural lordotic angle, but may be any angle suitable for use in the spine. The particular patient anatomy will generally determine whether a spacer like that shown in FIGS. 1-4 or in FIG. 5 will be required. However, a surgeon may employ one design or the other for other reasons.

FIGS. 6-9 depict an insertion tool 50 for use in inserting and positioning a prosthetic intervertebral spacer, for instance, above-described spacer 10, in the intervertebral disc space between two adjacent vertebra. As is more clearly shown in the exploded view of FIGS. 7 and 8, insertion tool 50 includes a grasping portion 52 having first and second arms 54a and 54b that are preferably capable of moving with respect to one another. In the particular embodiment shown, arms 54a and 54b act as spring clips having proximal ends attached to other portions of grasping portion 52 and distal ends between which the dimension can be varied. In other embodiments, arms 54a and 54b may be movable in other fashions, such as rotatable or the like. Tool 50 further includes a sleeve 56 having an inner surface 57 that is slidably disposed about grasping portion 52. A portion of inner surface 57 of sleeve 56 includes opposing surfaces that are preferably spaced apart by a dimension that is less than a resting dimension between the outer portions of arms 54a and 54b. This allows for the distance between arms 54a and 54b to be reduced upon sliding of the sleeve distally. This preferably allows for arms 54a and 54b to be in an initial position, such as separated by the resting dimension, where they are able to receive spacer 10, and where sliding of sleeve 56 causes arms 54a and 54b to affix to interface 26. In this regard, arms 54a and 54b each preferably include projections 58a and 58b, respectively, for positioning adjacent to the shoulder formed between neck portion 28 and lip portion 30 of interface 26. Moreover, arms 54a and 54b and projections 58a and 58b are preferably curved to properly mate with the curvature of interface 26 and therefore to allow rotation of spacer 10 with respect to tool 50. The rotational relationship between spacer 10 and tool 50 will be discussed more fully below.

Figure 6:
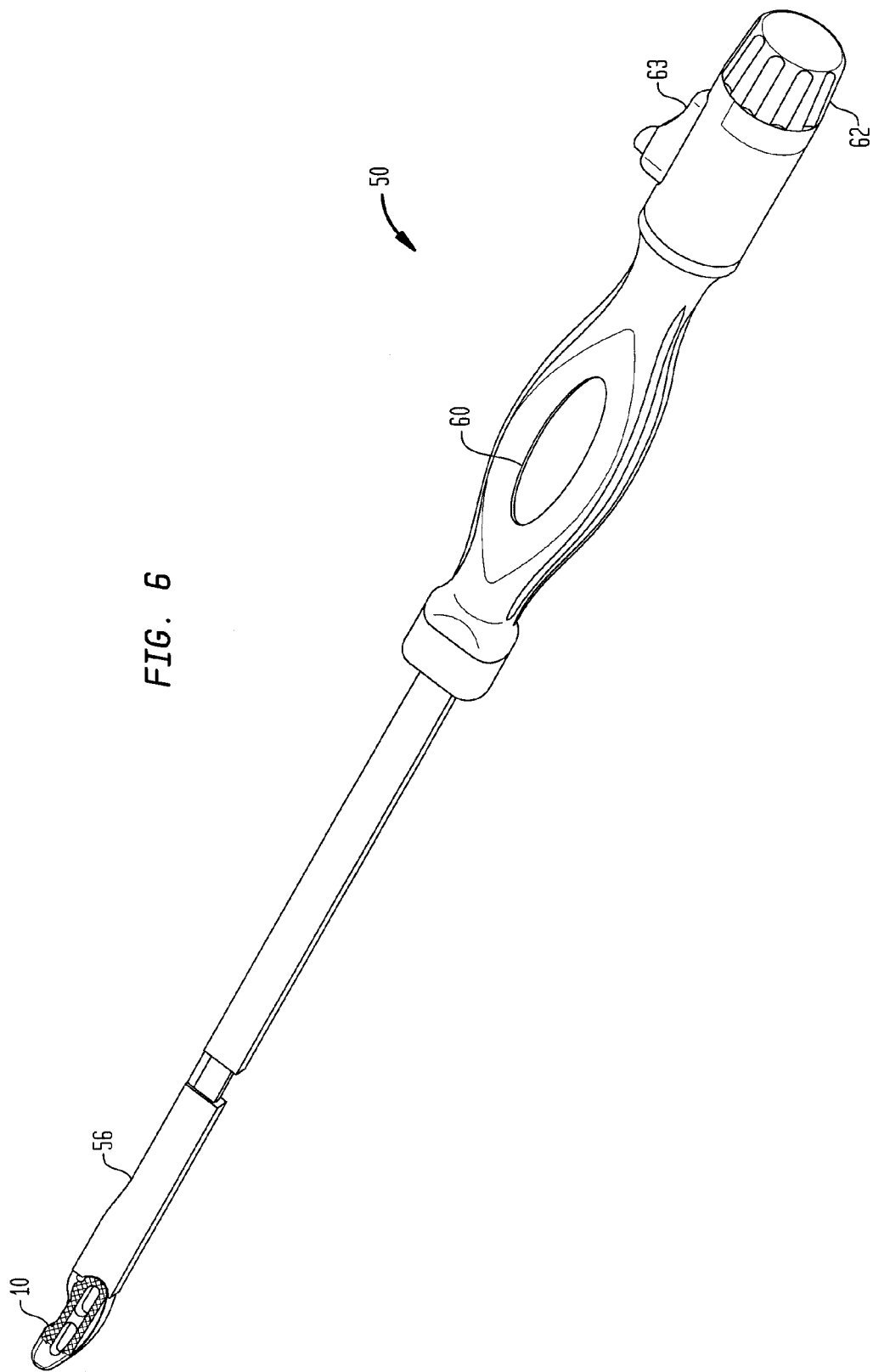
FIG. 6 is a perspective view of a surgical tool for use in inserting and positioning a prosthetic intervertebral spacer in accordance with one embodiment of the present invention.
Figure 7:
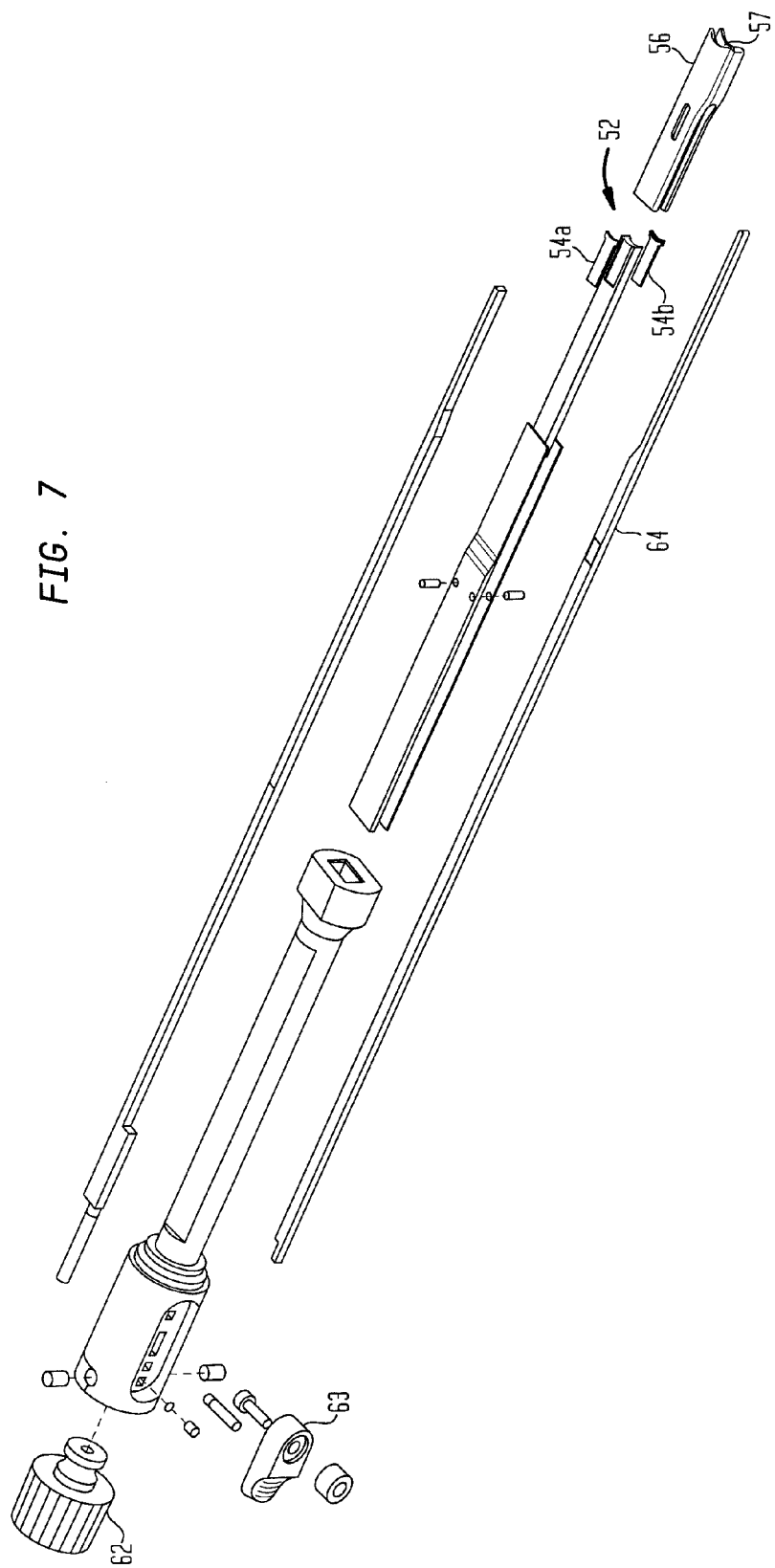
FIG. 7 is an exploded view of the insertion tool shown in FIG. 6.
Figure 8:
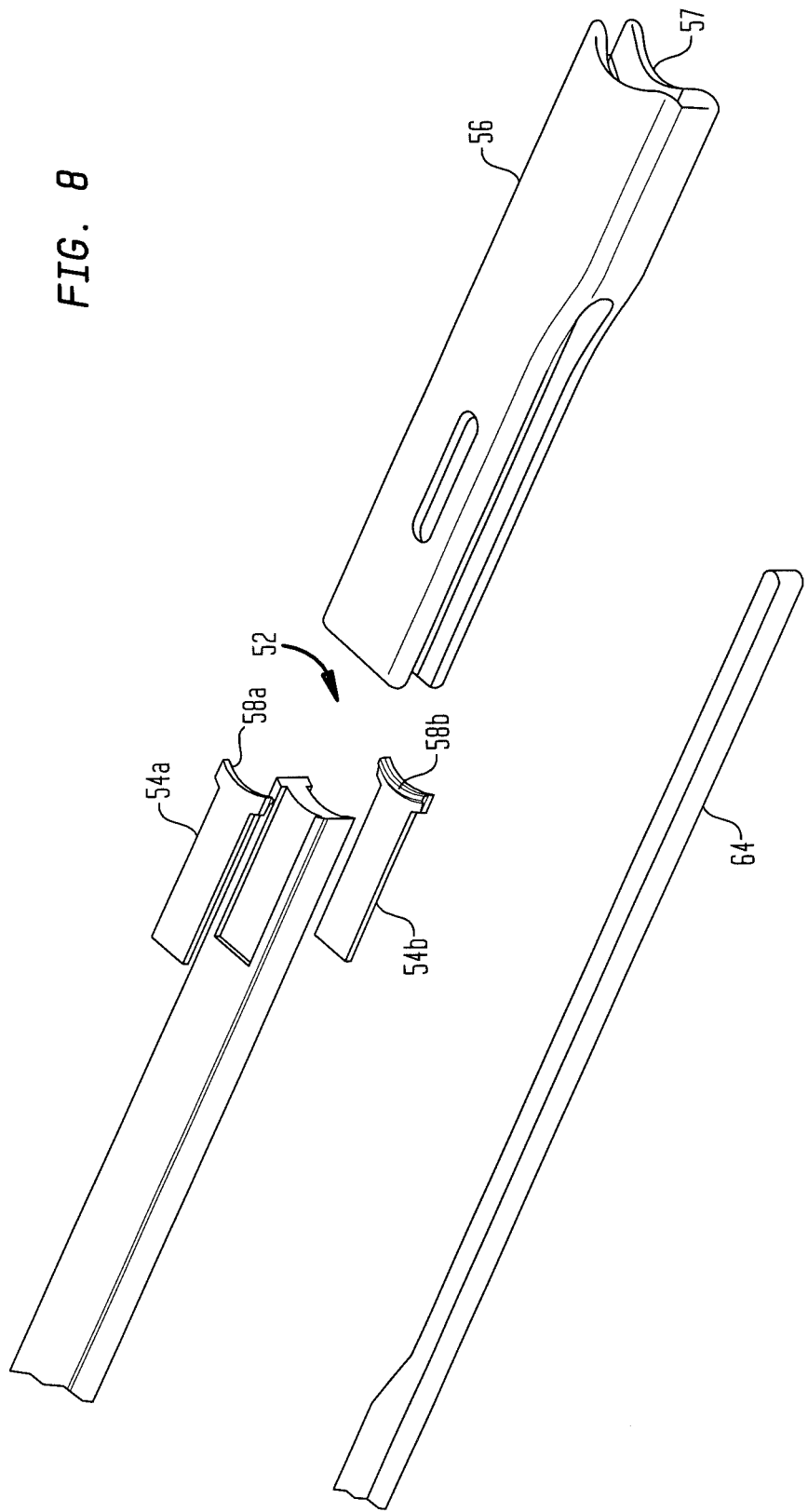
FIG. 8 is an enlarged exploded view of a portion of the view of FIG. 7.

As best shown in FIG. 6, tool 50 further includes a handle portion 60 connected to grasping portion 52. Handle portion 60 preferably further includes a sleeve actuator 62 for causing sliding movement of sleeve 56. In the embodiment shown, sleeve actuator 62 includes a rotatable knob, the rotation of which causes the sliding of sleeve 56. Handle portion 60 also preferably includes a rod actuator 63 for causing movement of a rod 64 (best shown in FIGS. 7 and 8) that acts as a rotational lock for spacer 10. In the embodiment shown, rod actuator 63 takes the form of a switch, the sliding of which causes movement of rod 64. Handle portion 60 also preferably includes a grip 66 that may be ergonomically shaped and formed with a material suitable for grasping by a surgeon.

Figure 9:
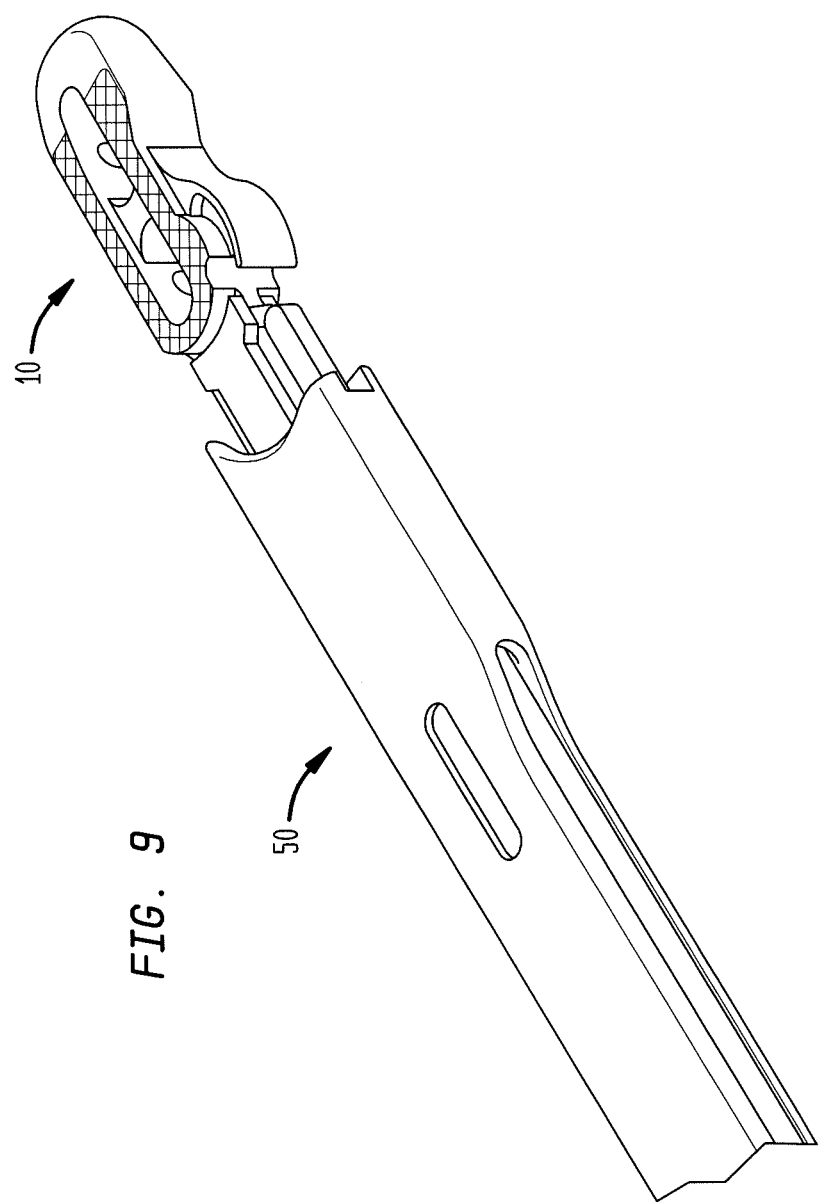
FIG. 9 is in illustration depicting an initial connection between the spacer shown in FIG. 1 and the insertion tool shown in FIG. 6.
Figure 10:
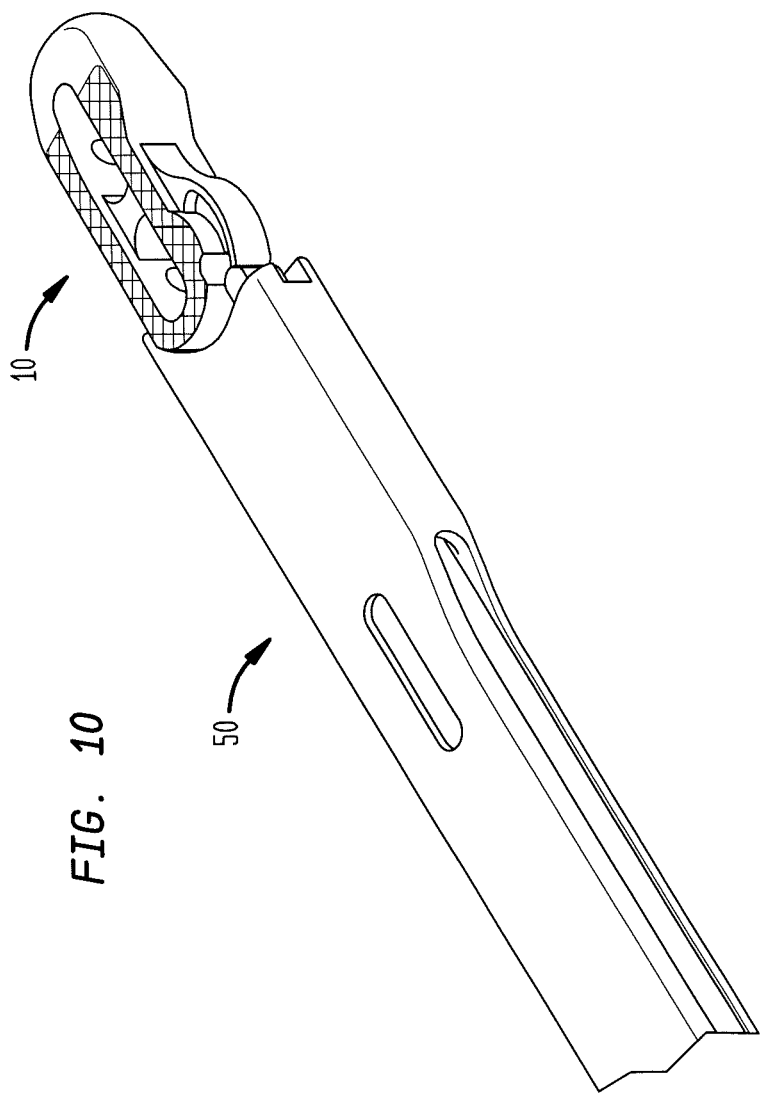
FIG. 10 is an illustration depicting the spacer and insertion tool construct shown in FIG. 9 with the insertion tool in a locked position.
Figure 11:
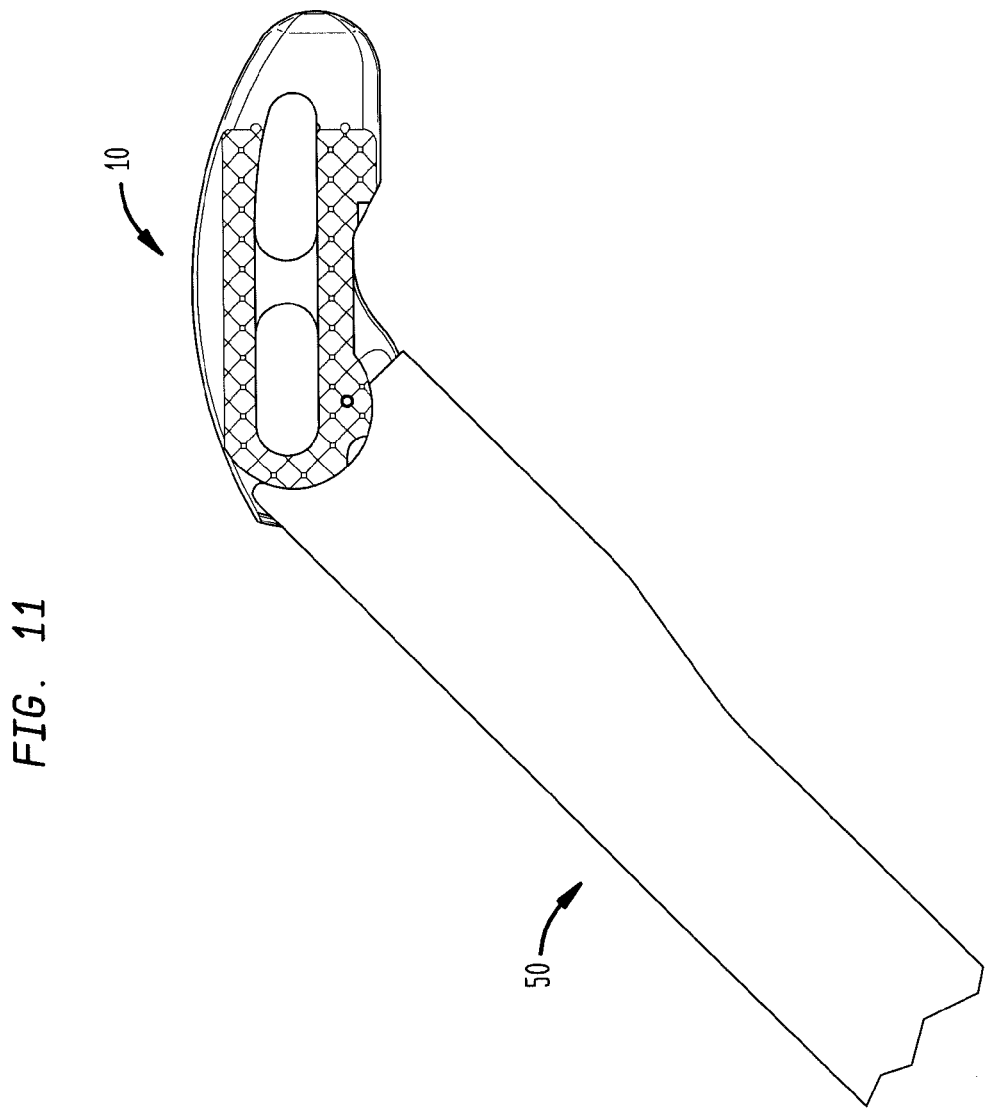
FIG. 11 is an illustration depicting the spacer and insertion tool construct shown in FIG. 9 with the spacer rotated with respect to the insertion tool.
Figure 12:
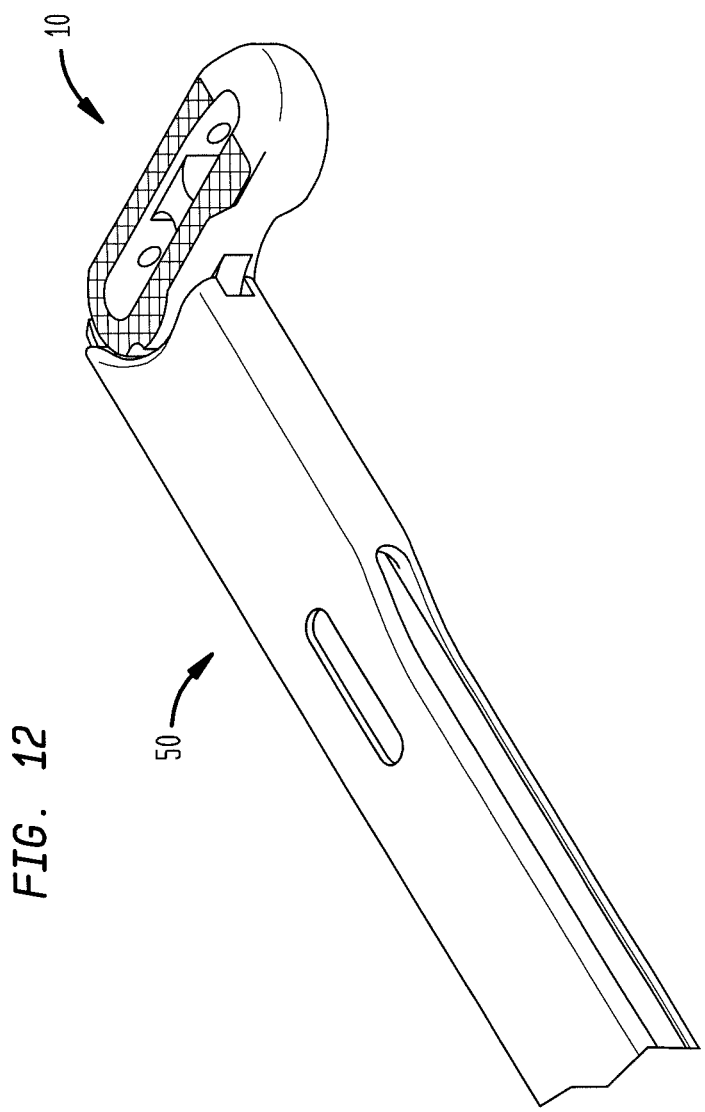
FIG. 12 is an illustration of the spacer and insertion tool construct shown in FIG. 9 with the spacer fully rotated with respect to the insertion tool.
Figure 13:
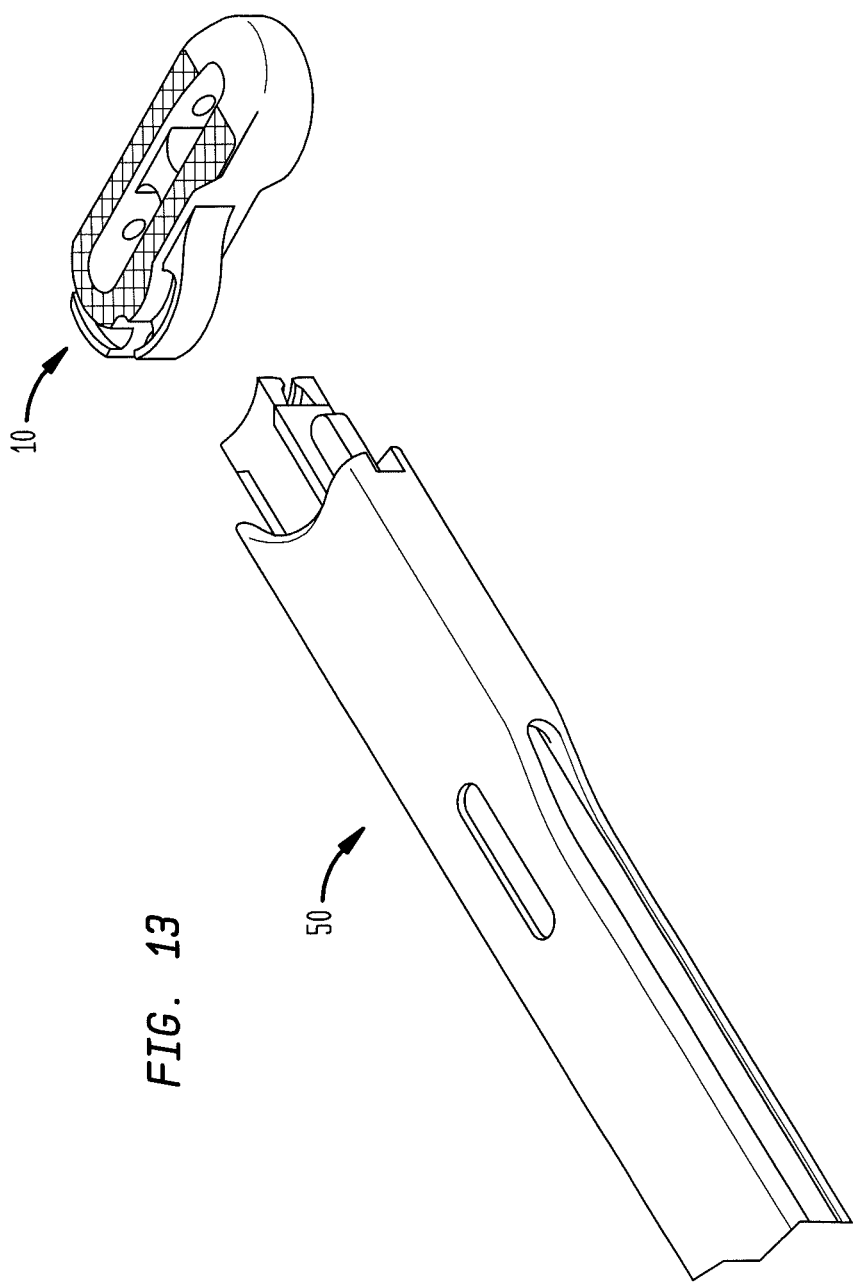
FIG. 13 is an illustration depicting the spacer and insertion tool construct shown in FIG. 9 with the spacer released from the insertion tool.

FIGS. 9-13 depict the mating relationship between spacer 10 and insertion tool 50. With reference to FIG. 9, the initial connection between spacer 10 and tool 50 is depicted. As noted above, arms 54a and 54b are preferably in an initial state suitable for receiving interface 26 of spacer 10. With reference to FIG. 10, the inserter is shown with sleeve 56 slid over arms 54a and 54b to affix spacer 10 to tool 50. In addition, rod 64 is shown deployed into notch 32. Thus, spacer 10 can neither be removed from nor rotated with respect to tool 50. FIG. 11 depicts spacer 10 rotated with respect to tool 50. Essentially, in FIG. 11, rod 64 has been disengaged from notch 32 through actuation of rod actuator 64. The arcuate nature of interface 26 and arms 54a and 54b allows for the rotation between the components. FIG. 12 depicts spacer 10 rotated at a maximum amount with respect to tool 50. This amount is approximately 80 degrees, but may be greater in other embodiments, including approximately 90 degrees. Where FIGS. 9 and 10 depicted the majority of tool 50 being connected with first segment 26a of interface 26, FIG. 12 depicts the majority of tool 50 being connected with second segments 26b due to the rotation of spacer 10 with respect to tool 50. Finally, FIG. 13 depicts spacer 10 having been released from tool 50 upon sliding of sleeve 56 in the opposite direction from which it is shown in FIGS. 10-12.

Figure 14:
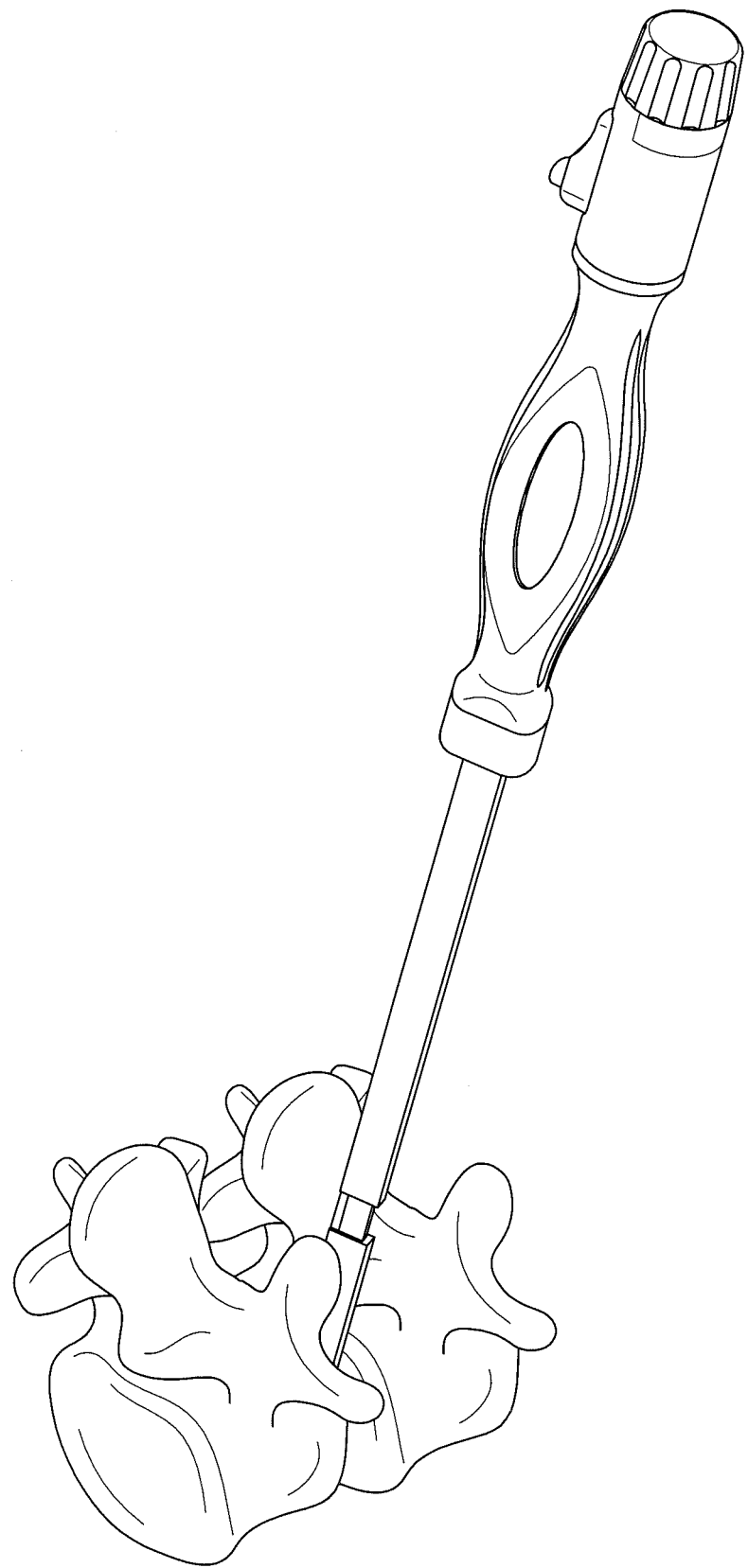
FIG. 14 is an illustration depicting the spacer and insertion tool construct shown in FIG. 9 in relation to an intervertebral space.
Figure 15:
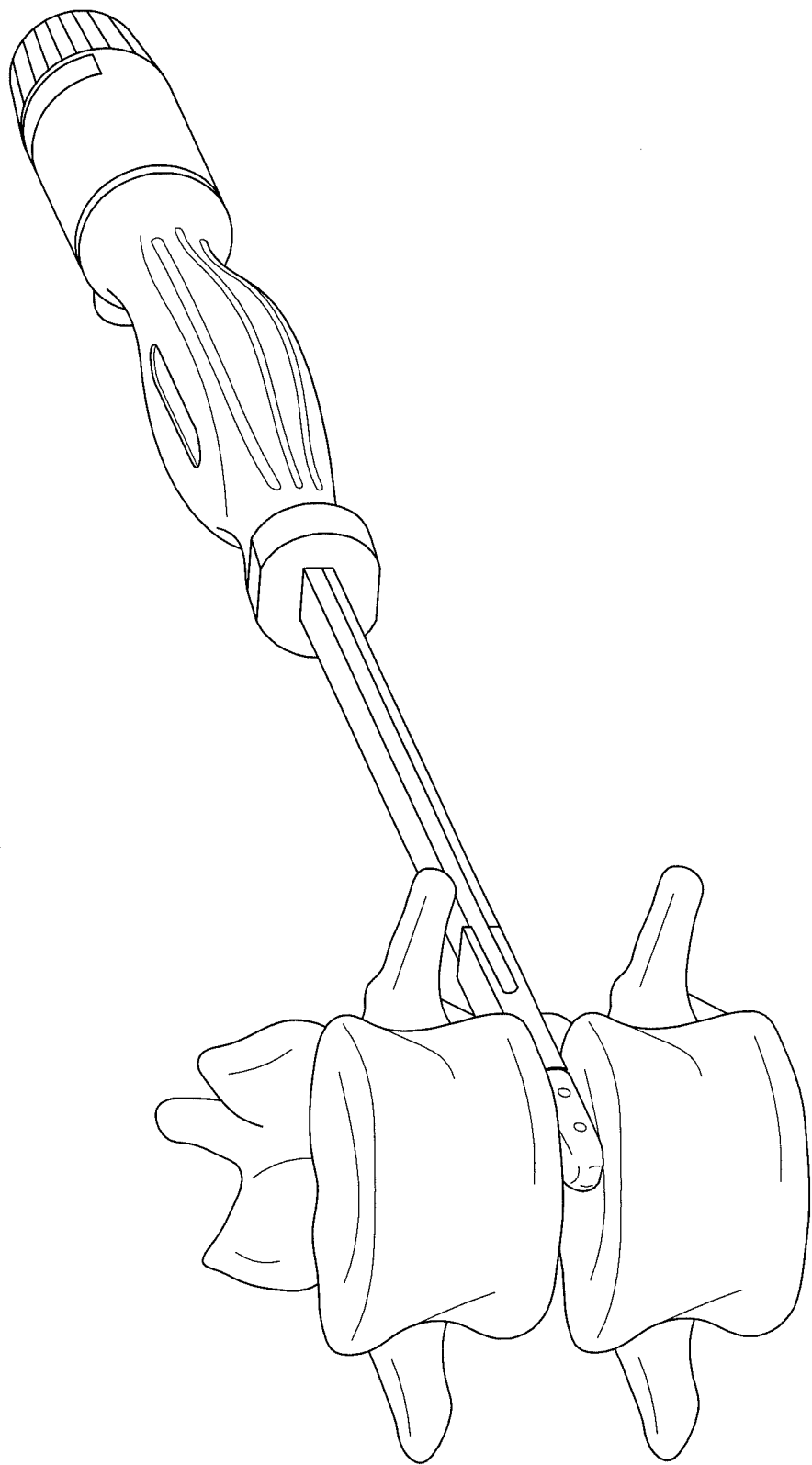
FIG. 15 is an illustration depicting the spacer and insertion tool construct shown in FIG. 9 in relation to the intervertebral space, with the spacer in a fully inserted position.

FIGS. 14 and 15 depict the spacer 10 and tool 50 construct discussed above in relation to two adjacent vertebral bodies in the spine of a human being. Although FIG. 14 depicts spacer 10 being inserted from a posterior aspect of the spine, spacer 10 may be inserted from any aspect. For instance, in other embodiments, spacer 10 is inserted from an anterior aspect of the spine. Likewise, although shown in FIG. 15 in a final position located in an anterior portion of the intervertebral disc space, spacer 10 may ultimately be disposed in many different areas of that intervertebral disc space. For example, spacer 10 may ultimately be implanted so as to be located in a posterior portion of the intervertebral space.

Figure 16D:
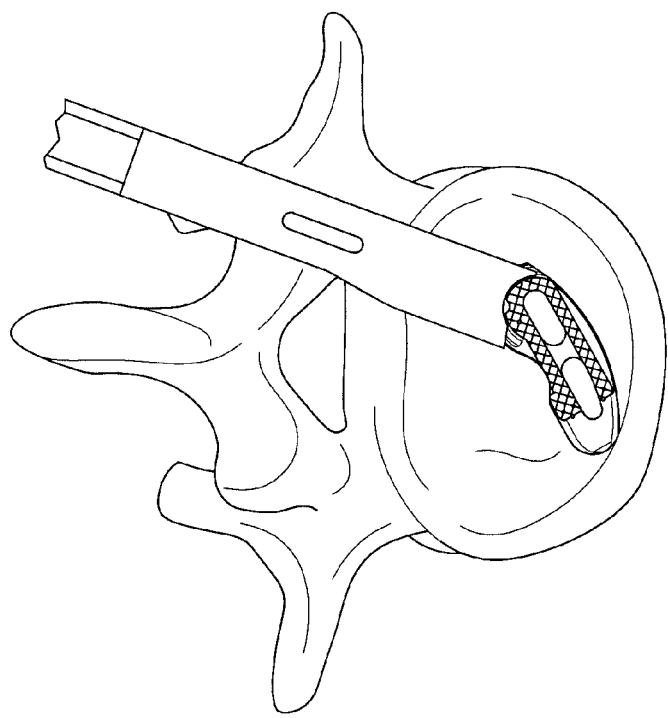
Figure 16C:
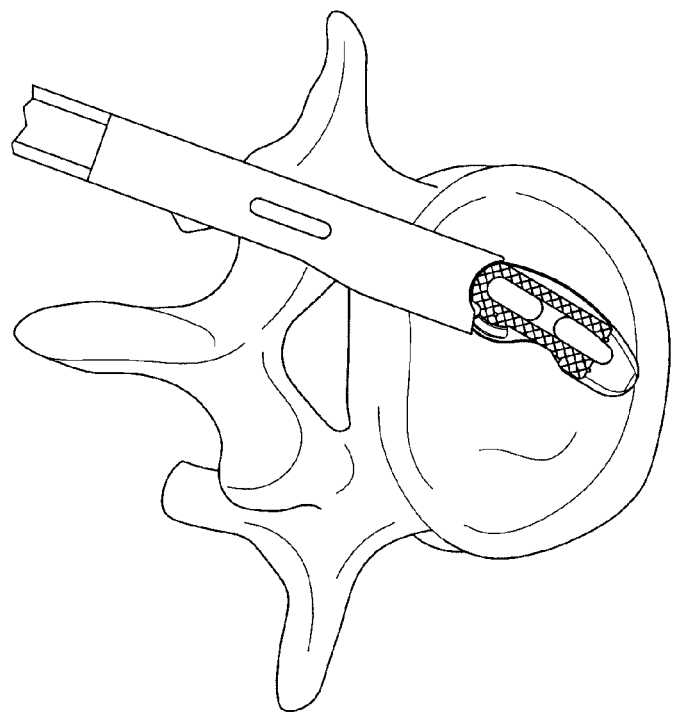
Figure 16E:
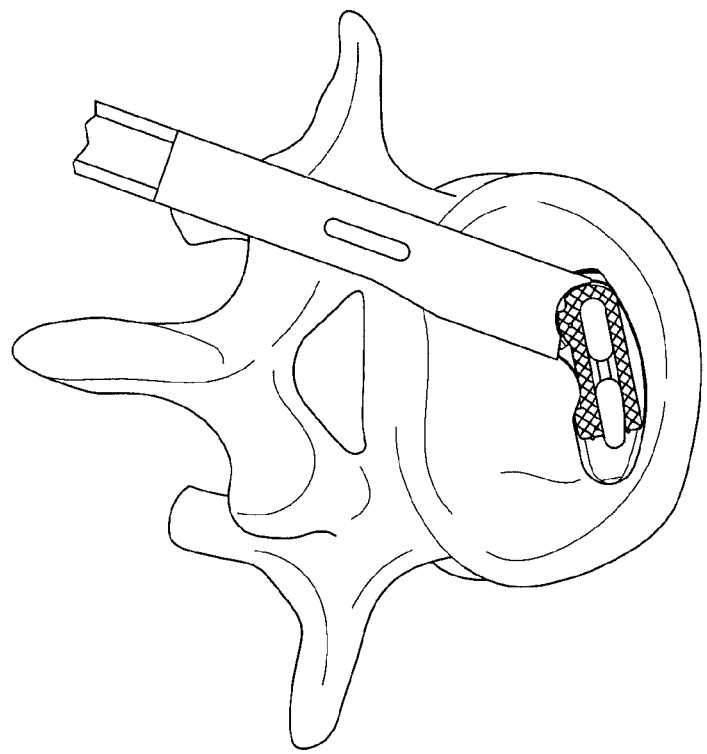
Figure 16F:
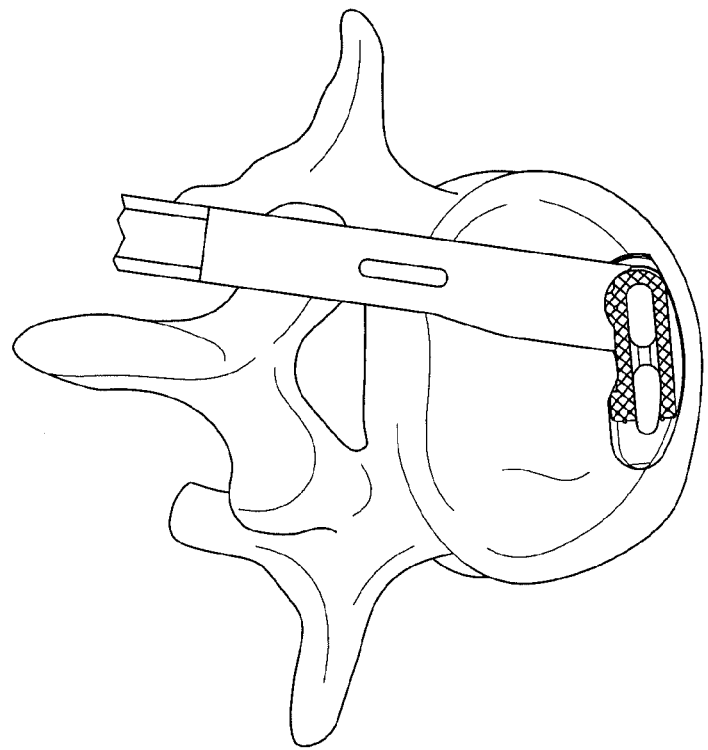
Figure 16G:
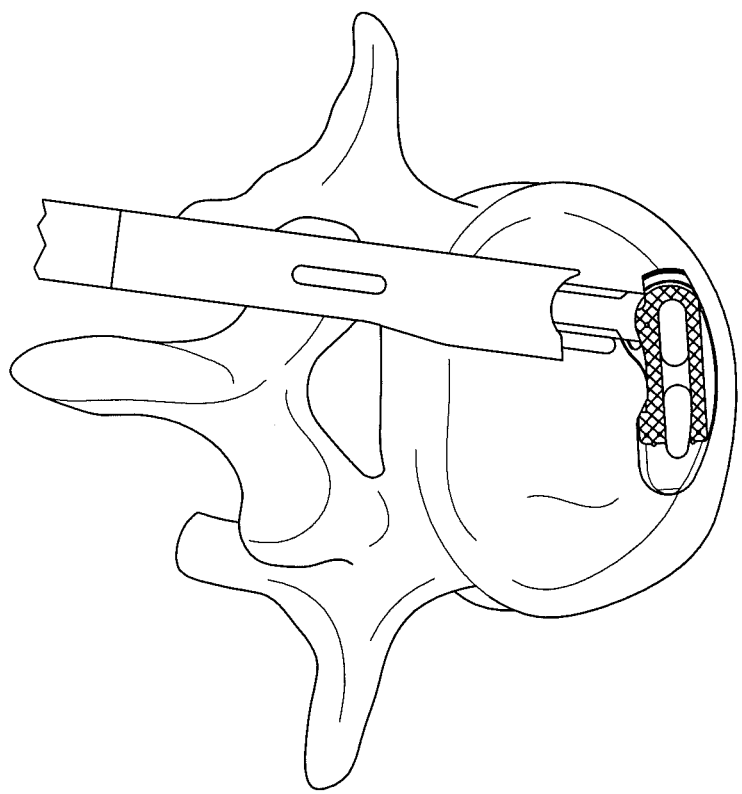

FIGS. 16a-16g depict in more detail one embodiment method of inserting and positioning spacer 10 in the intervertebral disc space between two adjacent vertebra with the use of tool 50. Prior to conducting the method shown in those figures, a surgeon preferably forms a hole through the annulus fibrosis of an intervertebral disc space, leaving a large amount of that anatomical feature untouched. The surgeon may then remove (through the formed hole or otherwise) certain material from the space in order to allow for spacer 10 to be inserted therein. Thereafter, as shown in FIG. 16a, the locked spacer 10 and tool 50 construct shown in FIG. 10 is inserted through the hole formed through the annulus fibrosis. Again, while this is shown in FIG. 16a as having occurred from a posterior lateral aspect, other entry aspects may be utilized in inserting spacer 10. Upon contact of spacer 10 with a remaining portion of the annulus fibrosis (see FIG. 16b) rod actuator 63 is actuated to withdraw the rotational lock provided by rod 64 being disposed within notch 32. Spacer 10 is then allowed to rotate with respect to tool 50 during further insertion of the construct within the space, as front end 14 engages the remaining portion of the annulus fibrosis. FIGS. 16c-16e depict subsequent and sequential steps in this insertion process. FIG. 16f depicts spacer 10 fully rotated with respect to insertion tool 50 and disposed in an anterior portion of the disc space where, in this embodiment, it shall remain. FIG. 16g depicts tool 50 being removed from spacer 10. This is due to operation of sleeve actuator 62 to slide sleeve 56 with respect to grasping portion 52. Spacer 10 is now in its final position and tool 50 can be removed from the space.

The methods of inserting spacer 10 may further include the steps of packing apertures 36a and 36b with bone growth inducing substances, such as bone morphogenetic proteins or natural bone materials. In embodiments in which spacer 10 includes a steering element, the rotation between spacer 10 and tool 50 may occur prior to engagement of spacer 10 with the remaining portion of the annulus fibrosis. In addition, it is to be understood that the tapered nose of front end 14 of spacer 10 preferably aids in the initial insertion of the spacer within the intervertebral disc space, as well as the cooperation of the spacer with the remaining portion of the annulus fibrosis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of inserting and positioning a prosthetic intervertebral spacer in an intervertebral disc space between two adjacent vertebrae, the method comprising the steps of:
    providing a spacer including a body and an interface, the body having a front end, a rear end, top and bottom surfaces, and a longitudinal axis, the interface defining a rail having a neck portion connected to and extending away from the rear end of the body, the rail further having a lip portion connected to the neck portion, the lip portion being wider than the neck portion in a direction extending between the top and bottom surfaces;
    engaging a tool to the rail;
    inserting the spacer at least partially into the intervertebral disc space by moving the tool along an insertion direction; and
    allowing the spacer to rotate with respect to the insertion direction within the intervertebral disc space while continuing to move the tool along the insertion direction, wherein upper and lower arms of the tool slide along the rail during rotation of the spacer.

2. The method of claim 1, wherein the tool maintains its engagement to the interface during the steps of inserting and allowing.

3. The method of claim 2, wherein the step of allowing the spacer to rotate includes allowing the front end to interact with an annulus fibrosus of an intervertebral disc to cause rotation of the spacer with respect to the insertion direction.

4. The method of claim 3, wherein the spacer is inserted such that the spacer is positioned in an anterior aspect of the intervertebral disc space.

5. The method of claim 3, wherein the spacer is inserted to a final position wherein the longitudinal axis of the spacer is perpendicular to the insertion direction.

6. The method of claim 5, wherein the longitudinal axis of the spacer is substantially parallel to a medial-lateral axis of the intervertebral disc space.

7. The method of claim 3, wherein the spacer is inserted such that the longitudinal axis of the spacer is rotated approximately 80 degrees with respect to the insertion direction.

8. The method of claim 3, wherein the step of allowing the spacer to rotate further includes allowing a steering element disposed on the front end of the spacer to mate with one of the two adjacent vertebral bodies to cause rotation of the spacer with respect to the insertion direction.

9. The method of claim 8, wherein the steering element is disposed at an angle with respect to the longitudinal axis.

10. The method of claim 8, wherein the steering element is a fin or a crease.

11. The method of claim 1, further comprising a step of forming a hole through only a portion of an annulus fibrosus while leaving the remainder of the annulus fibrosus intact, and wherein the step of inserting includes inserting the spacer through the hole.

12. The method of claim 1, wherein the insertion direction is substantially parallel to a posterior-anterior axis of the intervertebral disc space.

13. The method of claim 1, wherein the interface of the spacer includes a notch and the tool includes a rod engageable to the notch, further comprising a step of engaging the rod to the notch to prevent relative rotation between the spacer and the tool, and a step of disengaging the rod from the notch to allow relative rotation between the spacer and the tool.

14. The method of claim 13, wherein the allowing step takes place after the rod is disengaged from the notch.

15. The method of claim 14, wherein the spacer is at least partially inserted with the rod engaged to the notch and at least partially inserted with the rod disengaged from the notch.

16. The method of claim 1, wherein the body further includes at least one aperture extending between the top and bottom surfaces, the method further comprising a step of packing bone graft material into the at least one aperture.

17. The method of claim 1, wherein the front end of the spacer has frictional properties that are greater than frictional properties of the rear end of the spacer to aid in the rotation of the spacer within the intervertebral disc space.

18. A method of inserting and positioning a prosthetic intervertebral spacer in an intervertebral disc space between two adjacent vertebrae, the method comprising the steps of:
providing a spacer including a body and an interface, the body having a front end, a rear end, top and bottom surfaces, and a longitudinal axis, the interface defining a rail having a neck portion connected to and extending away from the rear end of the body, the interface including a notch, the rail further having a lip portion connected to the neck portion, the lip portion being wider than the neck portion in a direction extending between the top and bottom surfaces;
engaging a tool to the rail, the tool including a rod;
engaging the rod to the notch to prevent relative rotation between the spacer and the tool;
inserting the spacer at least partially into the intervertebral disc space by moving the tool along an insertion direction;
disengaging the rod from the notch;
inserting the spacer further into the intervertebral disc space after the disengaging step by moving the tool substantially along the insertion direction; and
allowing the spacer to rotate with respect to the insertion direction within the intervertebral disc space when the rod is disengaged from the notch while continuing to move the tool along the insertion direction.

19. The method of claim 18, further comprising a step of forming a hole through only a portion of an annulus fibrosus while leaving the remainder of the annulus fibrosus intact, and wherein the first step of inserting includes inserting the spacer through the hole.

20. The method of claim 18, wherein the step of allowing the spacer to rotate includes allowing the front end to interact with an annulus fibrosus of an intervertebral disc to cause rotation of the spacer with respect to the insertion direction.

21. The method of claim 20, wherein the tool maintains its engagement to the interface during the steps of inserting and allowing.

22. The method of claim 21, wherein the spacer is inserted such that the spacer is positioned in an anterior aspect of the intervertebral disc space.

23. The method of claim 21, wherein the spacer is inserted to a final position wherein the longitudinal axis of the spacer is perpendicular to the insertion direction.

24. The method of claim 23, wherein the longitudinal axis of the spacer is substantially parallel to a medial-lateral axis of the intervertebral disc space.

25. The method of claim 21, wherein the spacer is inserted such that the longitudinal axis of the spacer is rotated approximately 90 degrees with respect to the insertion direction.

26. The method of claim 18, wherein the allowing step includes allowing upper and lower arms of the tool to slide along the rail during rotation of the spacer.

27. The method of claim 18, wherein the front end of the spacer includes a steering element, and the step of allowing the spacer to rotate further includes allowing the steering element to mate with one of the adjacent vertebral bodies to cause rotation of the spacer with respect to the insertion direction.

28. The method of claim 27, wherein the steering element is disposed at an angle with respect to the longitudinal axis.

29. The method of claim 27, wherein the steering element is a fin or a crease.

30. The method of claim 18, wherein the insertion direction is substantially parallel to a posterior-anterior axis of the intervertebral disc space.

31. The method of claim 18, wherein the body further includes at least one aperture extending between the top and bottom surfaces, the method further comprising a step of packing bone graft material into the at least one aperture.

32. The method of claim 18, wherein the front end of the spacer has frictional properties that are greater than frictional properties of the rear end of the spacer to aid in the rotation of the spacer within the intervertebral disc space.

33. The method of claim 18, wherein the first step of inserting includes applying a force to the spacer along a first axis substantially parallel to the longitudinal axis of the spacer, and the second step of inserting includes applying a force to the spacer along a second axis forming an angle with the longitudinal axis of spacer of greater than zero degrees.

34. A method of inserting and positioning a prosthetic intervertebral spacer in an intervertebral disc space between two adjacent vertebrae, the method comprising the steps of:
providing a spacer including a body and an interface, the body having a front end, a rear end, top and bottom surfaces, and a longitudinal axis, the interface defining a rail having a neck portion connected to and extending away from the rear end of the body, the rail further having a lip portion connected to the neck portion, the lip portion being wider than the neck portion in a direction extending between the top and bottom surfaces;
applying a force to a tool engaged to the rail to move the spacer into the intervertebral disc space, the force being directed along an insertion direction; and
allowing the front end to interact with an annulus fibrosus of an intervertebral disc to cause rotation of the spacer with respect to the insertion direction while continuing to move the tool along the insertion direction.

35. The method of claim 34, further comprising steps of forming a hole through only a portion of an annulus fibrosus while leaving the remainder of the annulus fibrosus intact, and inserting the spacer through the hole.

36. The method of claim 34, wherein the engagement between the tool and the interface is maintained during the steps of applying and allowing.

37. The method of claim 34, wherein the allowing step includes allowing upper and lower arms of the tool to slide along the rail during rotation of the spacer.

38. The method of claim 34, wherein the interface of the spacer includes a notch and the tool includes a rod engageable to the notch, further comprising a step of engaging the rod to the notch to prevent relative rotation between the spacer and the tool, and a step of disengaging the rod from the notch to allow relative rotation between the spacer and the tool.

39. The method of claim 38, wherein the allowing step takes place after the rod is disengaged from the notch.

40. The method of claim 39, wherein the spacer is at least partially inserted with the rod engaged to the notch and at least partially inserted with the rod disengaged from the notch.

41. The method of claim 34, wherein the step of allowing includes allowing a steering element disposed on the front end of the spacer to mate with an adjacent vertebral body to cause rotation of the spacer with respect to the insertion direction.

42. The method of claim 41, wherein the steering element is disposed at an angle with respect to the longitudinal axis.

43. The method of claim 41, wherein the steering element is a fin or a crease.

44. The method of claim 34, wherein the step of applying includes the insertion direction being substantially parallel to the longitudinal axis of the spacer, and further comprising a step of applying a second force to the spacer along a second axis forming an angle with the longitudinal axis of greater than zero degrees.

* * * * *